United States Patent
Golenski et al.

(10) Patent No.: US 11,094,413 B1
(45) Date of Patent: Aug. 17, 2021

(54) TIME-BASED RESOURCE ALLOCATION FOR LONG-TERM INTEGRATED HEALTH COMPUTER SYSTEM

(71) Applicant: KAIROI HEALTHCARE STRATEGIES, INC., San Francisco, CA (US)

(72) Inventors: John D. Golenski, San Francisco, CA (US); David J. Flanagan, San Francisco, CA (US)

(73) Assignee: KAIROI HEALTHCARE STRATEGIES, INC., San Francisco, CA (US)

(*) Notice: Subject to any disclaimer, the term of this patent is extended or adjusted under 35 U.S.C. 154(b) by 0 days.

(21) Appl. No.: 16/863,434

(22) Filed: Apr. 30, 2020

Related U.S. Application Data

(60) Provisional application No. 62/989,299, filed on Mar. 13, 2020.

(51) Int. Cl.
| | |
|---|---|
| *G16H 40/20* | (2018.01) |
| *G16H 10/60* | (2018.01) |
| *G16H 50/30* | (2018.01) |
| *G16H 50/70* | (2018.01) |
| *G16H 40/67* | (2018.01) |
| *G06F 21/60* | (2013.01) |
| *G16H 50/20* | (2018.01) |
| *G06F 16/25* | (2019.01) |

(52) U.S. Cl.
CPC ........... *G16H 40/20* (2018.01); *G06F 16/258* (2019.01); *G06F 21/602* (2013.01); *G16H 10/60* (2018.01); *G16H 40/67* (2018.01); *G16H 50/20* (2018.01); *G16H 50/30* (2018.01); *G16H 50/70* (2018.01)

(58) Field of Classification Search
CPC ........ G16H 40/20; G16H 40/67; G16H 10/20; G16H 10/60; G16H 50/30; G16H 50/20
USPC .............................................................. 705/2
See application file for complete search history.

(56) References Cited

U.S. PATENT DOCUMENTS

| | | | |
|---|---|---|---|
| 7,789,828 B2 | 9/2010 | Clapp | |
| 8,626,521 B2 | 1/2014 | Brown et al. | |
| 8,862,448 B2 | 10/2014 | Holmes et al. | |
| 9,529,974 B2 | 12/2016 | Li et al. | |
| 10,354,211 B1 | 7/2019 | Pilkington et al. | |
| 2004/0122709 A1* | 6/2004 | Avinash | G16H 10/60 705/2 |
| 2009/0093686 A1 | 4/2009 | Hu et al. | |
| 2010/0312581 A1* | 12/2010 | Wachtell | G06Q 50/24 705/3 |
| 2013/0080134 A1 | 3/2013 | Donovan et al. | |
| 2015/0106119 A1 | 4/2015 | McCafferty | |
| 2016/0103963 A1 | 4/2016 | Mishra | |
| 2016/0210427 A1 | 7/2016 | Mynhier et al. | |
| 2017/0177822 A1 | 6/2017 | Fogel | |

(Continued)

OTHER PUBLICATIONS

Web archive of HL7FHIR http://hl7.org/fhir/R4/ captured on Mar. 11, 2020 (3 pages).

(Continued)

*Primary Examiner* — Hiep V Nguyen
(74) *Attorney, Agent, or Firm* — Pillsbury Winthrop Shaw Pittman LLP

(57) ABSTRACT

Provided is a system configured to allocate healthcare resources for population health management using time values, health scores, or health condition labels stored in a population of records.

22 Claims, 4 Drawing Sheets

(56) References Cited

U.S. PATENT DOCUMENTS

| | | |
|---|---|---|
| 2018/0075207 A1 | 3/2018 | Schmidt |
| 2018/0113982 A1 | 4/2018 | Asthana et al. |
| 2018/0240547 A1 | 8/2018 | Albert |

OTHER PUBLICATIONS

International Search Report and Written Opinion for related International Patent Application No. PCT/US2021/022084, dated Jun. 29, 2021 (13 pages).

\* cited by examiner

TIME-BASED RESOURCE ALLOCATION FOR LONG-TERM INTEGRATED HEALTH COMPUTER SYSTEM

CROSS-REFERENCE TO RELATED APPLICATIONS

This patent application claims the benefit of U.S. Provisional Patent Application 62/989,299, titled TIME-BASED RESOURCE ALLOCATION FOR LONG-TERM INTEGRATED HEALTH SYSTEM, filed 13 Mar. 2020. The entire content of the earlier-filed application is hereby incorporated by reference for all purposes.

BACKGROUND

The present disclosure relates generally to population health management computer systems and, more specifically, to interpretable techniques for allocating resources with the same.

The practice of computer-implemented decision-making is useful in various resource-limited environments such as population health management. Computer-implemented resource allocation may be especially useful in cases for allocating resources such as provider time or outreach time to population groups distributed throughout a geographic region. Appropriate resource allocation may increase the number and magnitude of positive, long-term outcomes for large populations.

SUMMARY

The following is a non-exhaustive listing of some aspects of the present techniques. These and other aspects are described in the following disclosure.

Some aspects include a process that includes obtaining, with the computing system, a population of patient records, where each respective record of the population of patient records comprises a respective set of time values, and where a respective set of health scores associated with a respective patient identifier, and where a respective healthcare resource identifier, and where each time value of the respective set of time values indicates an event occurrence time, and where the event occurrence time is associated with an update to the respective set of health scores. The process may include assigning, with the computing system, a plurality of priority scores to the population of patient records using a prioritization heuristic based on a prioritization criterion, wherein the population of patient records comprises a first patient record and a second patient record, and wherein using the prioritization heuristic comprises: determining a first elapsed time based on a first time value of the first patient record, wherein the first patient record comprises a first health score, and wherein the first time value and the first health score are associated with the prioritization criterion. The process may include determining a first priority score associated with the first patient record based on the first elapsed time and the first health score. The process may include determining a second priority score associated with the second patient record based on a second time value and a second health score, wherein the second patient record comprises the second time value and the second health score, and wherein the second time value and the second health score are associated with the prioritization criterion. The process may include sorting, with the computing system, the plurality of priority scores into a sequence of priority scores to determine a sequence of records from the population of patient records. The process may include obtaining a utilization schedule of a healthcare resource based on a resource identifier, wherein the resource identifier is determined based on a record selected from the sequence of records.

Some aspects include a tangible, non-transitory, machine-readable medium storing instructions that when executed by a data processing apparatus cause the data processing apparatus to perform operations including the above-mentioned process.

Some aspects include a system that includes one or more processors and memory storing instructions that, when executed by the processors, cause the processors to effectuate operations of the above-mentioned process.

BRIEF DESCRIPTION OF THE DRAWINGS

The above-mentioned aspects and other aspects of the present techniques will be better understood when the present application is read in view of the following figures in which like numbers indicate similar or identical elements.

Figure 1:
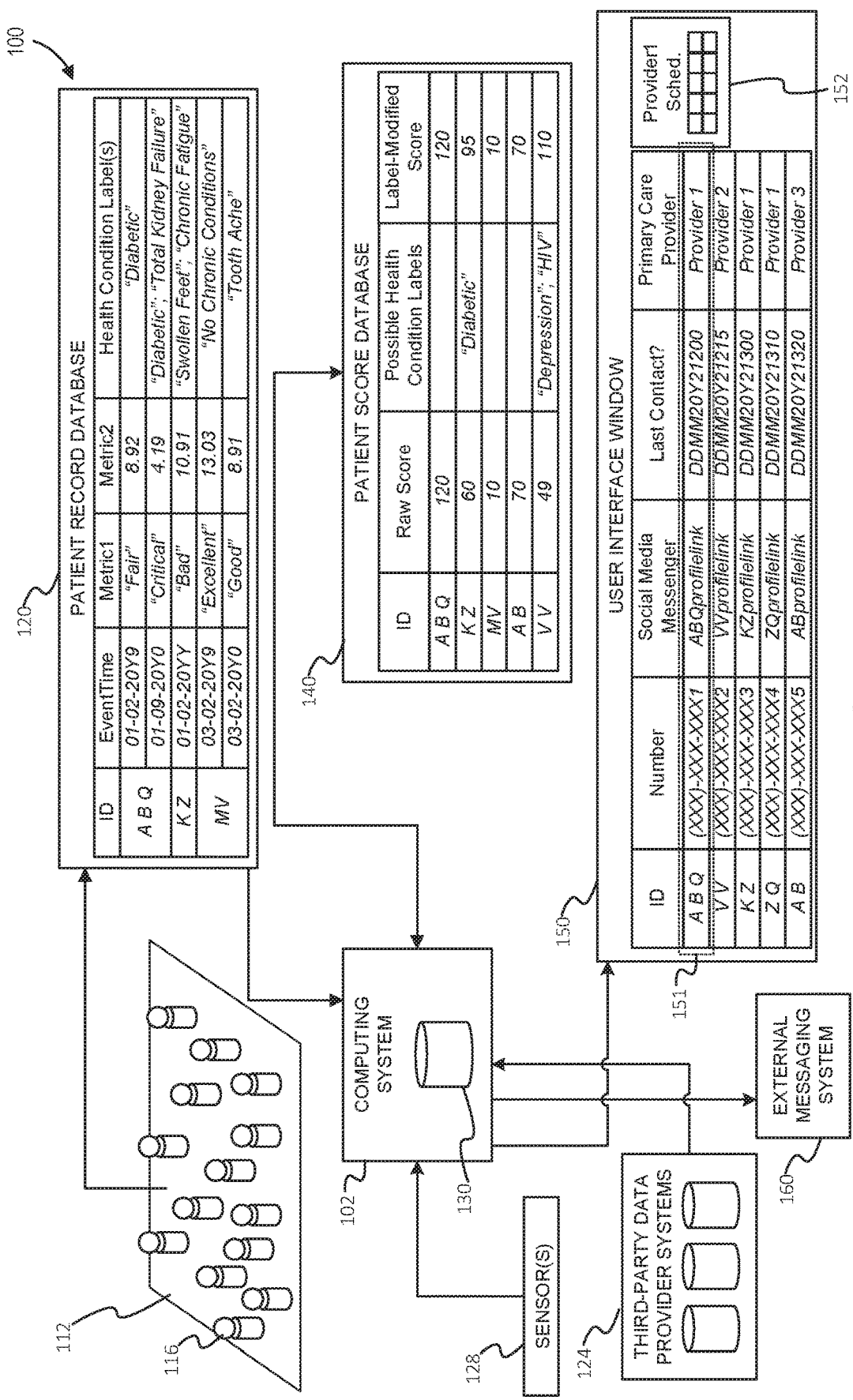
FIG. 1 is a schematic diagram of a first computing environment in which various components for health resource allocation in an integrated medical system may be implemented with the present techniques, in accordance with some embodiments.

While the present techniques are susceptible to various modifications and alternative forms, specific embodiments thereof are shown by way of example in the drawings and will herein be described in detail. The drawings may not be to scale. It should be understood, however, that the drawings and detailed description thereto are not intended to limit the present techniques to the particular form disclosed, but to the contrary, the intention is to cover all modifications, equivalents, and alternatives falling within the spirit and scope of the present techniques as defined by the appended claims.

DETAILED DESCRIPTION

To mitigate the problems described herein, the inventors had to both invent solutions and, in some cases, just as importantly, recognize problems overlooked (or not yet foreseen) by others in the field of computer science and human-computer interaction. Indeed, the inventors wish to emphasize the difficulty of recognizing those problems that are nascent and will become much more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

Existing computer systems for resource allocation in a healthcare setting are cumbersome in certain use cases. In many cases, these systems require a user to interact with multiple software applications to perform different, but logically related activities, like assessing patient (or other entity) need in one application, and scheduling doctor time in a different application. Often, these systems rely on manual cross-referencing operations to triage patients, assess which healthcare resources are associated with them, and allocate the corresponding healthcare resources to them. In various real-world settings, these operations may rely on disparate or otherwise unconnected datasets. Further, there is often substantial cognitive load for the user imposed by the need to navigate different applications into related states and convey information therebetween. None of which is to suggest that fragmented approaches like these are disclaimed, as some of the present techniques may be implemented across multiple, distinct software applications. While some examples of operations described in this disclosure are described as applying to patients or patient records, some embodiments may apply the operations described in this disclosure to other entities or other entity records.

Many health-care professionals rely on a heterogenous set of applications to prioritize and schedule patient care. Often, they use different software applications, organization-specific scripts, and the manual efforts of healthcare staff to analyze and coordinate health issues in a large population (e.g., with more than 1,000 patients). This patchwork of tools may fail to address preventable health issues related to a significant population segment that is not likely to visit a healthcare provider until they experience a significant amount of preventable health decline. While a proactive approach to this demographic of non-visiting patients may be successful in significantly reducing this effort, the number of patients, their qualitative similarities, and the requirements for complex social interactions to induce a healthcare visit can make contact attempts futile for large populations. Even systems that include mechanisms to initiate contact attempts with vulnerable population segments suffer from significant hurdles with respect to inconsistently-labeled data, incorrectly-labeled data, missing data, and unlabeled data.

As discussed below, some embodiments may provide an improved user interface that increases the efficiency of computer users when performing resource allocation operations, such as scheduling operations for patients and healthcare providers. The improved user interface may integrate disparate data from both a set of patient records and a set of healthcare resource utilization schedules. The improved user interface may concurrently present the patient record data and utilization schedule on a display device and may dynamically change the displayed utilization schedule or otherwise access the utilization schedule based on a selected patient. It should be emphasized, though, that not all embodiments necessarily provide these advantages, as there are several independently useful ideas described herein, and some implementations may only apply a subset of these techniques.

Typical mental processes for resource allocation in a healthcare setting are not suitable for operations at scale, even when executed by a computer system. Often, time complexity scales with the square of the number of members of the set being compared, e.g., in big-O notation, this is expressed as $O(n^2)$, which holds for many typical pairwise comparison approaches. Many existing triaging algorithms rely on pairwise heuristic approaches to determine the priorities of multiple patients or other entities. Such pairwise operations may include iteratively comparing pairs of patients with each other for prioritization purposes. While such pairwise heuristics may be sufficient for a small number of patients, such operations become computationally expensive to scale due to the exponential growth in the number necessary comparisons as the number of patients increase (e.g., more than 1000 patients, more than 10,000 patients, or more than 100,000 patients may become infeasible to compare in this manner even with a computer). Furthermore, the number of computations required to compare patients with each other may be exponentially increased for scenarios requiring calculations to take into account additional relationships, such as the effect of visit times and the nature of visit times. That said, some embodiments may implement pairwise comparisons when applying some of the approaches discussed below.

Some embodiments mitigate these scaling issues. Some embodiments compute a priority score and rank or sort by this score as described further below. Some embodiments may reduce the computational complexity of triaging when allocating healthcare resources across a large population of patients or other entities. It should be emphasized, though, that embodiments are not limited to systems affording these benefits, as some embodiments may implement other innovative techniques described below without also applying the above-noted approaches to mitigate scaling challenges.

Embodiments may assign priority scores to patients (or other organisms of interest) for attempting to initiate contact to fill openings in a schedule of a health-care resource (like a doctor or medical device) or performing other resource allocation activities. Some embodiments may obtain a large population of records (e.g., more than 1,000) associated with the health of patients or other individuals, where each record may include one or more time values and a set of health scores. In some embodiments, the time values of a health record for a person may indicate a health-related event occurrence time during which one or more health metric of the person is updated. Such health-related events may include a doctor's visit by the person, a diagnostic testing event, a telehealth event over the internet, or the like. The time value may be associated with a health score of the record, where a health score may be associated with a health metric and may be determined from a measurement or a qualitative assessment. These health scores may be used to detect one or more possible health conditions and, in response, assign one or more health condition labels to a patient. The system may then use the time values, health scores, health condition labels, or some combination thereof to determine a priority score for a patient.

A priority score may then be used to allocate healthcare resources such as contact attempt resources, remote provider resources, equipment resources, or the like. As discussed further below, a sequence of priority scores may be used to select a patient or other entity to contact and provide a contact attempt resource with a contact value associated with the patient corresponding to the priority score. Alternatively, or in addition, the priority scores or values used to determine the priority scores may be used to determine outcomes associated with different prioritization heuristics or criteria, which may then be used to update a selected prioritization heuristic or criteria.

FIG. 1 is a schematic diagram of a first computing environment in which various components for health resource allocation in an integrated medical system may be implemented with the present techniques, in accordance with some embodiments. The geographic region 112 may include a set of patients 116, each of whom may have one or more records in a patient record database 120. Each patient record may be obtained from one or more healthcare facilities, independent healthcare providers, or directly reported by a patient of the set of patients 116. In some embodiments, the patient record database 120 may include a set of patient records, where each record of the set of patient records is associated with a patient identifier. For example, a first record for patient "A B Q" may include a patient identifier such as the patient's name, a randomly assigned alphanumeric value, a Social Security number, or the like. The first patient record may also include a set of health scores associated with a set of health metrics. For example, a first health metric may include an organ coloration scored using a visual heuristic, and a second health metric may include a blood test using a chemical concentration as a measurement heuristic. In some embodiments, a record in the patient record database 120 may include a set of time values associated with a set of health-related event occurrence times. For example, a first patient record may include a first time value associated with a first physical health checkup and a second time value associated with a second physical health checkup. In some embodiments, a record of the patient record database 120 may include or otherwise be associated with a set of health condition labels. For example, a first patient record may include the health condition labels, "diabetic" and "total kidney failure." In some embodiments, a health score or health condition label may be associated with a time value, where the time value may indicate when the health score or health condition label was first recorded or categorized.

In some embodiments, a computing system 102 may store or otherwise access the patient record database 120 to determine a set of priority scores. As further discussed below, the computing system 102 may access the patient record database 120 via an application program interface (API). For example, the computing system 102 may be a cloud computing application that is isolated from a data center storing the patient record database 120, where the computing system 102 may access the patient record database 120 via an API using an encryption key. In some embodiments, the computing system 102 may reference one or more identifiers or records of patients stored in the patient record database 120 to determine additional health scores or health condition labels associated with one or more patients stored in a set of third-party data provider systems 124. The set of third-party data provider systems 124 may include geographic information systems, other electronic health records, healthcare facility records, or the like. For example, the computing system 102 may access a third-party electronic medical record system to obtain additional health condition labels for the patient "A B Q" that was not found in the patient record database 120. In some embodiments, the computing system 102 may receive sensor measurements from a set of sensors 128, where each sensor measurement may be associated with a patient identified in the patient record database 120. In some embodiments, a corresponding record for the patient may be updated based on one or more sensor measurements from one of the sensors of the set of sensors 128. For example, the set of sensors 128 may include a mobile phone or tablet device used by the patient "A B Q," where the mobile phone or tablet may measure a body temperature and send the measurement to be used as a health score by the computing system 102 for determining a priority score for the patient "A B Q."

In some embodiments, the computing system 102 may use a set of time values, a set of health scores, or a set of health condition labels to determine a plurality of priority scores for patients identified in the patient record database 120. As further discussed below, assigning a priority score to a patient may include the use of one or more prioritization heuristics, where a prioritization heuristic includes a set of computer-readable instructions to determine a priority score. In some embodiments, the computing system 102 may categorize a patient with one or more system-detected health condition labels for a patient based on the set of health scores or existing health condition labels stored in the patient's record or otherwise associated with the patient's record. For example, the computing system 102 may predict that a patient "K Z" is a diabetic and, in response, assign the health condition label "diabetic" to the corresponding record of the patient as a system-detected health condition label, where a system-detected health condition label may be tagged or otherwise indicated as a non-diagnosed health condition label. By using both explicitly-diagnosed health conditions and system-detected health conditions, a prioritization heuristic may be able to provide useful information for determining a priority score that may otherwise be missing in conventional healthcare resource allocation systems while still maintaining a level of interpretability useful for various downstream operations. In addition, the distinction between system-detected health condition labels and health condition labels obtained from other patient records increases the likelihood that one or more of the operations described in this disclosure may be performed without violating medical protocols or regulations.

In some embodiments, the computing system 102 may sort a plurality of priority scores into a sequence of priority scores to determine a sequence of records to then use to display or send to an API. As further discussed below, various sorting methods may be used and may depend in part on the prioritization heuristic used. The sorting method may sort by a descending order when priority scores are determined using a prioritization heuristic that assigns higher scores to patients that are likely to require more immediate care. For example, if a prioritization heuristic is used to determine a numeric score to indicate priority, where a higher numeric score indicates a greater need for attention, some embodiments may sort the plurality of priority scores in descending order to determine a sequence of priority scores. The patient information stored in the records associated with the top 10 greatest priority scores may then be displayed or otherwise used for other operations. Alternatively, the sorting method may sort by an ascending order, which may be useful if priority scores are determined using prioritization heuristics that assign lower scores to patients that are likely to require greater amounts of healthcare resources or require more immediate care. Alternatively, the sorting method may sort priority scores by their difference from a specific target prioritization value or an interval of values.

In some embodiments, the computing system 102 may send a subset of records or identifiers associated with the subset of records to an API of an external computer program or electronic device. In some embodiments, the sequence of records determined from the sequence of priority scores may be used to display a list of patients in a user interface window 150 based on their respective priority scores. The list of patients in the user interface window 150 may include a set of patient identifiers and contact information for each of the set patient identifiers. For example, the patient "A B Q" may be listed in the user interface window 150 along with a phone number associated with the patient "A B Q" and a social media account name of the patient "A B Q."

In some embodiments, the computing system 102 may include a connection with an external messaging system 160 to enable contact with a patient. The user interface window 150 may include a user interface element such as a hyperlink, a button, a slidable element, or the like. For example, each entry in the column titled "Social Media Messenger" of the user interface window 150 may include a hyperlink associated with a patient's account in a social media profile, where clicking on the hyperlink may open a chat window to the patient via a messaging application. In some embodiments, interacting with the user interface element may result in the computing system 102 sending a message including a sequence of text, a contact identifier associated with a patient, and a signature key associated with the identifier to an API of the external messaging system 160. Upon receipt of the message, the external messaging system may authenticate the message using the signature key and send a message containing the sequence of text to the entity identified by the contact identifier. The external messaging system 160 may include a distributed application such as a proprietary voice-over-IP application, a computer program based on an application-layer protocol such as an internet relay chat (IRC) protocol, a text-based messaging system using a cell-based control channel(s) such as a short message service (SMS), a social media messaging system of a social network, some combination thereof, or the like.

In some embodiments, the user interface window 150 may also include a set of previous contact attempt times. For example, a patient may have been contacted on January 1, and a set of previous contact attempt times in the user interface window 150 may indicate that a contact attempt was made on this date. In some embodiments, the user interface window 150 may include a user interface element that allows a patient to be removed from a patient list shown in the user interface window 150. For example, a user may be able to click on a patient identifier on a list of patients to indicate that the patient had been contacted. In response, the patient may be removed from the patient list shown in the user interface window 150. In some embodiments, the user interface window 150 may also include one or more health scores associated with a health metric of the corresponding patient.

In some embodiments, the user interface window 150 may include one or more healthcare resource identifiers associated with a patient, such as a primary care provider identifier. As further discussed below, some embodiments may include instructions to integrate a list of patients with one or more scheduling systems by transmitting healthcare resource identifiers that may then be used to obtain a utilization schedule of the healthcare resource associated with the healthcare resource identifier. A utilization schedule of a healthcare resource may be obtained in various forms, such in the form of a ".csv" file, ".ics" file, or the like, and may indicate the times during which a healthcare resource is available or unavailable for use. In some embodiments, the user interface may dynamically populate or otherwise display a utilization schedule for a healthcare resource associated with a patient that was previously not displayed in response to a user clicking on, tapping on, or otherwise interacting with a user interface element associated with the patient. For example, after a user clicks on the row 151, the resource allocation system (or data sent from the resource allocation system to the user interface) may cause the user interface to display a utilization schedule 152. In some embodiments, the data for the utilization schedule 152 may be obtained directly from the resource allocation system. Alternatively, or in addition, data for utilization schedule 152 may be obtained from a third-party system, such as a third-party scheduling system, after an API of the third-party system receives a request for the utilization schedule. Furthermore, in some embodiments, the utilization schedule may also be responsive to interactions by the user and may be used to update scheduling data stored in a local persistent memory or stored in an external application via an API.

While not shown, some embodiments may display a plurality of healthcare resource identifiers in association with a patient identifier. For example, some embodiments may display a care facility identifier on the user interface window 150 in place of or in addition to a primary care provider identifier. In some embodiments, some or all of the utilization schedules of each of the plurality of healthcare resource identifiers may be displayed. For example, after clicking on a first patient name, a first utilization schedule of an associated healthcare provider and a second utilization schedule of an MM machine may be displayed for a user to view or otherwise use.

Figure 2:
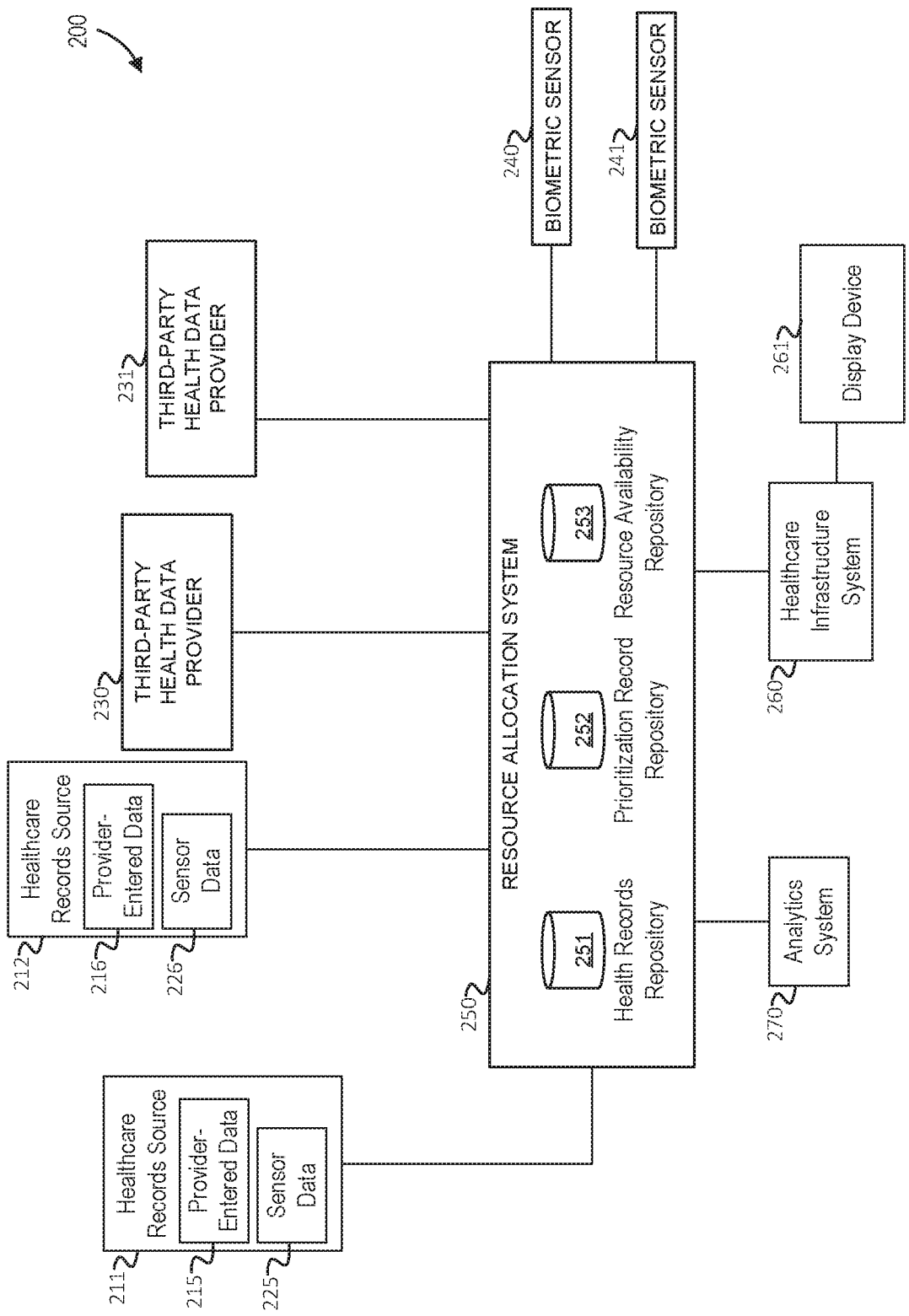
FIG. 2 illustrates a computing environment in which various prioritization infrastructure may be implemented with the present techniques, in accordance with some embodiments.

FIG. 2 illustrates a computing environment in which various prioritization infrastructure may be implemented with the present techniques, in accordance with some embodiments. In some embodiments, some or all of the above-describe techniques may be implemented in a computing environment 200. Each of the healthcare record sources 211-212 may provide patient records to a health records repository 251 of a resource allocation system 250, where the patient records may include provider-entered data 215-216 or sensor data 225-226. In some embodiments, the provider-entered data 215-216 may include quantitative data such as weight, analog-measured iris measurement, or the like. Alternatively, or in addition, the provider-entered data 215-216 may include categorical data such as health condition labels, coloration, or the like. For example, the provider-entered data 215 sent to the health records repository 251 may include the health condition labels "pre-diabetes" and "schizophrenia," where the health condition labels may be stored in or otherwise associated with a first patient record. Data collected by the sets of sensors 225-226 can include digital outputs from devices such as heart rate monitors, ultrasound devices, radiological devices, hematology analyzers, chemistry analyzers, blood gas analyzers, coagulation analyzers, electrolyte analyzers, immunoassay analyzers, urinalysis analyzers, or the like. In some embodiments, some or all of the sensor data 225-226 may be wirelessly transmitted to the resource allocation system 250 from their respective sensor devices. As discussed further below, data from the health records repository 251 may be used to generate or otherwise update a prioritization record repository 252. Furthermore, as further discussed below, the resource allocation system 250 may use a set of operations to allocate healthcare resources to patients based on data from the health records repository 251, the prioritization record repository 252, or the resource availability repository 253.

In some embodiments, third-party health data providers 230-231 may provide additional patient data to update one or more of the patient records stored in the health records repository 251. Alternatively, or in addition, the third-party health data providers 230-231 may add additional patient records to the health records repository 251. In some embodiments, conflicting data or duplicative data from the third-party health data providers 230-231 may be reconciled before, during, or after storage in the health records repository 251 by merging or deleting a set of conflicting or duplicative records or values stored in the set of conflicting or duplicative records. In some embodiments, biometric sensors 240-241 may provide additional biometric measurements or other health measurements to the health records repository 251. The sensor-acquired health measurements from the biometric sensors 240 or 241 and their corresponding measurement times may also be used to update the health records repository 251 or the prioritization record repository 252.

In some embodiments, the transfer of data from the third-party health providers 230-231 or the biometric sensors 240 or 241 may be encrypted or fuzzified to protect the identities or data values of entities associated with the data. In some embodiments, operations to encrypt or fuzzify the data may comply with established information transfer protocols established to satisfy government regulations such as the Health Insurance Portability and Accountability Act (HIPAA). For example, some embodiments may request permission from a patient or other entity identified by a record stored in a database of the third-party health provider 230 to acquire or share the data stored in the record. The permission or request may be sent via one or more various communication media, such as via a phone call, text message, an application operating on a computing device controlled by the entity, or the like. For example, some embodiments may send a request for permission to a patient via a smartphone application, where a patient may provide permission by pressing a button titled "I ACCEPT" of a graphic user interface of the smartphone application.

In some embodiments, the computing environment 200 includes the resource allocation system 250 configured to receive data from any of the above-described components. The resource allocation system 250 may be executed on a single computing device, a local server, a distributed computing network operated by a set of local servers, a cloud-based platform or service, some combination thereof, or the like. In some embodiments, the resource allocation system 250 may be configured to determine and store patient health information, patient identity information, or other information related to a person in a health records repository 251. The resource allocation system 250 may then use the health records repository 251 to determine a set of priority scores and store the priority scores and any other corresponding information in the prioritization records repository 252. Alternatively, or in addition, the resource allocation system 250 may store the priority scores or other corresponding information in other ways, such as in a data array stored in non-persistent memory, in another data repository such as the health records repository 251, or the like.

In some embodiments, the resource allocation system 250 may be configured to determine and store resource availability data in the resource availability repository 253. The resource availability data may include utilization schedules, healthcare resource locations, healthcare resource capabilities (e.g., diagnostics, treatments, etc.), or the like. For example, the resource availability repository 253 may include a first record for a healthcare provider that includes a provider name, a provider identifier, a three-month utilization schedule of the provider, a medical specialty of the provider, and a set of geographic locations at which the provider may work. The resource allocation system 250 may store resource data provided from various internal or external sources in the healthcare availability repository 253. For example, the resource allocation system 250 may obtain the utilization schedules of healthcare providers across multiple hospitals, clinics, and private practices by first loading data from an internal database of providers. The resource allocation system 250 may then obtain the utilization schedules of healthcare providers of external entities from messages sent by externally-managed data systems to an API of the resource allocation system 250. In some embodiments, the messages from the externally-managed data systems may be pulled from the externally-managed data systems, where pulled data is provided in response to a request sent by the resource allocation system 250 or an associated system managed by the resource allocation system 250. Alternatively, the messages encoding healthcare resource availability data may be pushed to the resource allocation system 250. For example, the resource allocation system 250 may be integrated with a data-sharing application shared by a plurality of independent medical institutions, where the data-sharing application may push messages storing equipment utilization schedules across a 200-kilometer radius to the resource allocation system 250 at 5 AM each day.

In some embodiments, the resource allocation system 250 may further include or communicate with a healthcare infrastructure system 260 that includes software to display text and graphics on a display device 261. As discussed further below, one or more prioritized patients may be selected based on the priority scores determined using the resource allocation system 250. In response, the information from the records of the selected patients, such as patient contact information, may be sent to the display device 261 for display via the healthcare infrastructure system 260. In addition, as further discussed below, prioritization information may be sent to the analytics system 270 to determine one or more updates to a set of prioritization criteria or prioritization weights based on population statistics or relationship scores determined from the priority scores and associated outcome measurements.

Figure 3:
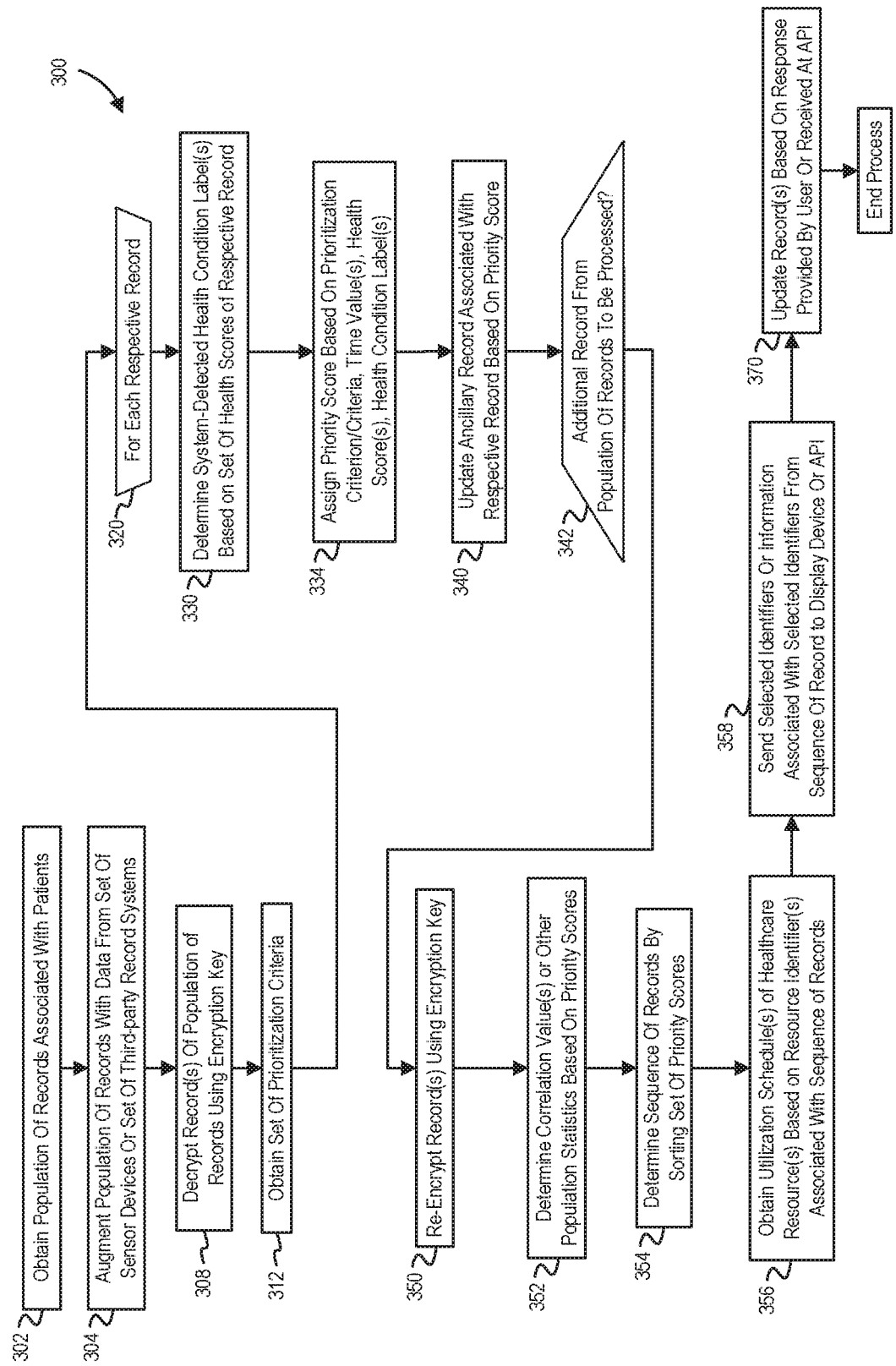
FIG. 3 is a flowchart of a process for health resource allocation in an integrated medical system, in accordance with some embodiments.

FIG. 3 is a flowchart of a process for health resource allocation in an integrated medical system, in accordance with some embodiments. FIG. 3 is a flowchart of processes that may be implemented in the computing environments of FIG. 1 to send sorted patient information to an electronic health system, in accordance with some embodiments. For example, the process may execute one or more routines in the computing environment 100. In some embodiments, the various operations of the process 300 may be executed in a different order, operations may be omitted, operations may be replicated, additional operations may be included, some operations may be performed concurrently, some operations may be performed sequentially, and multiple instances of the process 300 may be executed concurrently, none of which is to suggest that any other description herein is limited to the arrangement described. In some embodiments, the operations of the process 300 may be effectuated by executing program code stored in one or more instances of a machine-readable non-transitory medium, which in some cases may include storing different subsets of the instructions on different physical embodiments of the medium and executing those different subsets with different processors, an arrangement that is consistent with use of the singular term "medium" herein.

The process 300 may include obtaining a population of records associated with patients, as indicated by block 302. In some embodiments, obtaining the population of records may include querying a database of the computing system. For example, the resource allocation system may be executing on a computing system that includes a data storage device storing the population of records in a database. In some embodiments, obtaining the population of records may include sending a request to an API of a data system storing the population of records. For example, the resource allocation system may be executing on a set of data centers of a cloud computing environment, and the resource allocation system may send a request to a commercial data store that includes the population of records. Some embodiments may obtain, store, and augment the population of records using methods that are in compliance with regulations such as HIPAA. For example, some embodiments may use HIPAA-compliant end-to-end encryption when obtaining the population of records or use HIPAA-compliant full disc encryption when storing the population of records.

In some embodiments, obtaining the population of records may include transforming one or more records to be compatible with the resource allocation system. For example, a record of the population of records may store a blood type as a string value "A+," while one or more operations of the process 300 may require that the blood type be stored as a categorical value. During a data transformation operation, one or more values may have its data type changed, may be rounded to a different value, may be deleted, may be renamed, or the like. For example, a blood pressure of 180 mmHg may be converted into a category type "critically high." Alternatively, or in addition, one or more new health scores may be added to a record based on one or more existing health scores of a record. For example, a blood pressure risk may be assigned to each record of a population of records, where the risk value may be based on blood pressure measurements and a patient age.

A set of format transformation heuristics may be used to convert obtained records into a version of the records that are compatible with a resource allocation system. In some embodiments, a format transformation heuristic from the set of format transformation heuristics may be selected based on a stored data format. For example, the resource allocation system may determine a first population of records is stored in a first data format, determine a computer-implemented format transformation heuristics based on the first data format, and implement the format transformation heuristics to transform each of the first population of records into a second data format. A data format may be based on one or more specifications, such as the HL7 specification, the X12 specification, the Continuity of Care Record (CCR) specification, the Consolidated Clinical Document Architecture (CCDA) specification, the Fast Healthcare Interoperable Resource (FHIR) specification, or the like.

In some embodiments, the system may first check if a data format is using a pre-defined compatible data format based on a set of data format criteria, such as checking database compatibility using a built-in database tool or a custom-built data checking tool. For example, if the resource allocation system is configured to use a SQL database and the obtained population of records are already structured as a SQL database, some embodiments may prevent a data transformation heuristic from being used. In some embodiments, after detecting that one or more data format criteria or not satisfied, the system may implement a format transformation heuristic. For example, if the resource allocation system is configured to perform analysis on a SQL-based dataset after a determination that an obtained population of records is in a NoSQL data format, the resource allocation system may use a format transformation heuristic to convert the obtained population of records into a version of the population of records written as a SQL-based dataset. Some embodiments may indicate that a data format of a record in a population of records does not match a known data format and may send a warning message indicating that a transformation may be flawed.

In some embodiments, the format transformation heuristic may include one or more data size reduction operations to convert records into reduced-data versions of themselves. The format transformation heuristic may include a binning operation to simplify data analysis, where the binning operation may include approximating a numeric value to a lower-digit-count numeric value (e.g., rounding 3.51 to the value 3.5). In some embodiments, the data size reduction operation may include converting a higher number of categorical values into a lower number of categorical values. For example, the binning method may include converting the categorical values associated with the strings "excellent" and "good" stored in a set of obtained records into the singular categorical value "positive outcome." Alternatively, or in addition, the data size reduction operation may include replacing a numeric value with a categorical value.

The process 300 may include augmenting the population of records with data from a set of sensor devices or a set of third-party record systems, as indicated by block 304. A sensor device may include a biometric-specific device such as a blood-testing device, a urinalysis device, a saliva analysis device, or the like. For example, the sensor device may include a blood glucose testing device that transmits sensor measurements such as blood glucose measurements via an API to the resource allocation system. In some embodiments, the sensor device may be a smartphone or electronic tablet capable of making one or more biometric measurements such as a heart rate, a body temperature, an image of a body part, or the like. In some embodiments, some embodiments may receive sensor measurements with associated measurement times stored as time values. The sensor measurements obtained from a sensor device may be received at an API of the resource allocation system. For example, a device may send a message to an API of a resource allocation system operating under a Representational State Transfer (REST) architecture, where the message contains a signature value, a numeric value for the health metric "blood pressure," and a patient identifier or other entity identifier. After verifying the signature value, the system may add the numeric value to the record associated with the patient identifier or other entity identifier under the health metric "blood pressure."

A third-party record system may include a source of medical data, a source of identity data, a source of demographic data, or the like. In some embodiments, a third-party record system may include a data source that is not a part of the computing system operating the resource allocation system. In some embodiments, the resource allocation system may obtain additional health scores for patients (or other entities) by sending a set of requests to a third-party record system, wherein the request may include a set of patient identifiers. The resource allocation system may obtain additional health scores or additional health condition labels associated with the set of patient identifiers based on one or more request responses from the third-party record system. In some embodiments, the resource allocation system may add new patient records to the population of records in response to receiving one or more health scores or health conditions for a patient not encoded in the population of record.

In some embodiments, the process 300 may include decrypting one or more records of the population of records using an encryption key, as indicated by block 308. In some embodiments, the population of records may be obtained in an unencrypted format, removing a need to decrypt the population of records. Alternatively, population of records may be obtained in an encrypted format, such as the Data Encryption Standard (DES) encryption standard, the TripleDES encryption standard, the Rivest-Shamir-Adleman (RSA) encryption standard, the Advanced Encryption Standard (AES), the Twofish encryption standard, or the like. In some embodiments, the population of records may be only partially encrypted or not encrypted. Alternatively, the population of records may be completely encrypted. By storing some or all of the population of records in an encrypted form that requires an encryption key to unencrypt, the resource allocation system may reduce its vulnerability to malicious hacking attempts.

In some embodiments, the process 300 may include obtaining a set of prioritization criteria, as indicated by block 312. Obtaining a set of prioritization criteria may include obtaining the set of prioritization criteria from a user interface, a pre-set default, an API, or the like. The prioritization criteria may include a set of values that are interpretable by the receiving system to indicate one or more prioritization criteria. A prioritization criterion may include a criteria-selected health condition label, criteria-selected health score, criteria-selected health score range, criteria-selected health metric, or the like. For example, the resource allocation system may receive a message including the string "diabetes" encoded in a pre-specified format. In response, the resource allocation system may set the health condition label "diabetes" as a criteria-selected health condition label.

As discussed further below, the presence of a health-condition label that is a criteria-selected health condition label in a record may change the priority score associated with the record. In some embodiments, the set of prioritization criteria may include a plurality of health condition labels. Alternatively, the set of prioritization criteria may include only one health condition label. Alternatively, some embodiments may proceed to further operations of the process 300 without any prioritization criterion. In some embodiments, the set of prioritization criteria may include one or more thresholds for a quantitative, categorical, or Boolean value. For example, a prioritization criterion may include a condition that a quantitative health score for the health metric "potassium concentration" is greater than a potassium concentration threshold.

In some embodiments, the set of prioritization criteria maybe be updated based on an external data source. For example, some embodiments may send a request to a data store holding a set of prioritization criteria that includes a health score "130 mmHg" as a criteria-selected health score and a range value "10 mmHg" as a criteria-selected range. After receiving a response including the health score and the range, the resource allocation system may use these values as a criteria-selected health score interval ranging from 120 mmHg to 140 mmHg, which may then be used to determine a priority score based on a prioritization heuristic, as further discussed below.

In some embodiments, the process 300 may include performing one or more operations indicated by blocks 330, 334, 338, or 340 for each of the respective obtained records of the population of records, as indicated by block 320. In some embodiments, the process 300 may include determining a set of system-detected health condition labels based on the set of health scores of the respective record, as indicated by block 330. A respective patient record for a patient may include one or more health scores that indicate the existence of a health condition that may not necessarily be associated with the patient or the respective record. For example, a first record may include a blood pressure measurement, an eyesight measurement, a blood sugar measurement, a blood oxygen measurement, or the like. The health condition label "scoliosis" may be absent from the first record. However, the resource allocation system may apply a rule-based heuristic and determine that a set of health scores predict the possibility that the patient in the first record has scoliosis based on a computed probability value being greater than a threshold probability value. Alternatively, or in addition, the resource allocation system may determine one or more system-detected health condition labels for a patient using a combination of health scores and existing health condition labels stored in a record of the patient.

Various algorithms, heuristics, operations, or intelligent decision systems may be used to determine a system-detected health condition label. Some embodiments may include the use of symbolic AI systems, where a symbolic AI system may include instructions to provide outputs by applying one or more rules or by referencing values stored in a table based on the health scores or existing health condition labels. For example, a symbolic AI system may include instructions to assign the system-detected health condition label "prediabetes" to a patient associated with an A1C concentration equal to "6.0%" after applying a rule that instructed the resource allocation system to assign the label "prediabetes" to all patients associated with an A1C between 5.7% to 6.4%. The use of a symbolic AI system may allow for fast predictions or decisions, which may be especially advantageous when a population of records grows large. Additionally, a symbolic AI system may provide a significant degree of explainability or interpretability to one or more output decisions due to the ease by which decision outputs provided by symbolic AI systems may be tracked back to their corresponding rules, tables, or other referenceable elements. While the above discloses an embodiment that provides advantages based on the use of a symbolic AI system, not all embodiments necessarily provide the advantage or necessarily include a symbolic AI system, and some embodiments may lack the advantage in view of trade-offs or other advantages.

In some embodiments, the resource allocation system may use a learning system such as a supervised learning system, an unsupervised learning system, a semi-supervised learning system, a reinforcement learning system, or the like. The learning system may include a neural network trained to categorize a record as having one or more system-detected health condition labels. The neural network may be based on a large collection of nodes. Each node of a neural network may be connected with many other nodes of the neural network. Such connections can be enforcing or inhibitory in their effect on an activation state of one or more connected nodes. In some embodiments, each individual node may use a summing function that combines the values of its inputs together, where an input may be a health score, a health condition label, another value stored in or otherwise associated with a patient record, a computed result based on any of the above, or the like. In some embodiments, each connection (or the node itself) may use a threshold function such that an input signal must surpass the threshold before the node propagates the signal to other nodes. A neural network system may be self-learning and trained, rather than explicitly programmed, and can perform significantly better in certain areas of problem-solving compared to other computer programs. In some embodiments, neural networks may include multiple layers (e.g., where a value traverses from front layers to back layers). In some embodiments, back-propagation techniques may be utilized by the neural networks, where forward stimulation is used to reset weights on the "front" nodes. In some embodiments, stimulation and inhibition for neural networks may be more free-flowing, with connections interacting in a more chaotic and complex fashion.

The neural network may include one or more types of neural network, such as a feedforward neural network, radial basis function neural network, self-organizing neural network, convolutional neural network, a recurrent neural network, modular neural network, some combination thereof, or the like. For example, some embodiments may use a trained feedforward neural network to determine a probability score for a patient having a condition such "Hyperthyroidism" based on a set of health scores of the patient and, in response to the probability score satisfying a threshold, assign the system-determined health condition label "hyperthyroidism" to the patient. By using a neural network to assign a health condition label, some embodiments may be able to provide additional prioritization refinement that may help increase resource allocation efficiency. In addition, relevant healthcare providers may be shown these system-detected health condition labels, which may allow for downstream verification of the health condition or refutation of the health condition. Furthermore, while the above discloses an embodiment that provides advantages based on the use of a neural network or other learning system, not all embodiments necessarily provide the advantage or necessarily include a neural network or other learning system, and some embodiments may lack the above-described advantages in view of trade-offs or other advantages.

In some embodiments, the resource allocation system may use a mixed symbolic learning system that includes both a trainable learning system and a symbolic AI system. For example, some embodiments may include a system that assigns a first health condition label based on a rule and then determines a categorical severity level associated with the first health condition label based on a trained neural network. Alternatively, or in addition, some embodiments may include a system that requires both a learning system and a symbolic AI system to agree on a health condition before classifying a patient as having that health condition. A mixed symbolic learning system may be advantageous in fields where explainable categories or decisions may be necessary due to technical, legal, or economic restrictions. Furthermore, while the above discloses an embodiment that provides advantages based on the use of a mixed symbolic learning system, not all embodiments necessarily provide the advantage or necessarily include a mixed symbolic learning system, and some embodiments may lack the above-described advantages in view of trade-offs or other advantages.

In some embodiments, the resource allocation system may use a natural language processing (NLP) system to determine a system-detected health condition label. For example, a record may include one or more free-text entries written by a healthcare provider. The NLP system may be used to analyze the free-text entries to determine whether any additional diagnoses were made that were not recorded as a health condition label associated with a record. For example, a free-text entry of a first record may include the string sequence, "patient is likely to have Alzheimer's, further testing recommended." The resource allocation system may be used to analyze the string sequence, extract the term "Alzheimer's," determine that the health condition label "Alzheimer's" is not associated with the record, and, in response, associate the health condition label "Alzheimer's" with the patient record.

The NLP system may include the use of one or more language models based on transfer-learning implementations, where training weights and learning parameters obtained from a set of training activities may be used for other activities. Various language models may be used, such as the Bidirectional Encoder Representations from Transformers (BERT) model, XLNet model, RoBERTa model, DistilBERT model, TransformerXL model, GPT-2 model, or the like. When using an NLP system, various types of word embedding systems may be used, such as word2vec, GloVe, or fastText. For example, some embodiments may use a BERT model to determine a health condition label based on a free-text entry in a patient record and determine a probability value that the free text indicates the patient has the possible health condition based the written text (e.g. "patient is likely to have condition1") or not have the possible health condition (e.g., "patient is not showing signs of condition1"). In response to the probability value satisfying a threshold value, the resource allocation system may assign the possible health condition to the patient as a system-detected health condition label.

In some embodiments, the set of system-detected health condition labels may be distinguished from a set of health condition labels originally obtained from an internal or external data storage. The distinction may come as an additional field of the label, or as a separate association type, or as an additional tag associated with the set of system-detected health condition labels, or the like. The distinction between the set of system-detected health condition labels the set of health condition labels obtained from an operation described for block 302 or block 304 may be used when determining a priority score for the record or when reporting results made by the resource allocation system to an API or a user (e.g. via a graphic display, a stream of text, or the like). By making such a distinction, the resource allocation system may reduce the risk of an unverified diagnosis of a patient's condition being made by an unauthorized entity while still taking advantage of health scores to provide greater prioritization details.

In some embodiments, the process 300 may include assigning a priority score in association with the record based on the set of prioritization criteria, a set of time values, a set of health scores, or a set of health condition labels of the respective record, as indicated by block 334. Various prioritization heuristics may be used to assign a priority score to a patient based on the values stored in or otherwise associated with the record identifying the patient. A priority score may be categorical or quantitative and may be used to determine how to allocate a healthcare resource. A healthcare resource may include a healthcare provider or use of the healthcare provider's time, a healthcare facility or use of time spent in the healthcare facility, a piece of equipment or use of the equipment, outreach time, laboratory testing time, an amount of time spent scheduling use of a healthcare resource, or the like. For example, a healthcare resource may include time spent scheduling patients for appointments with a healthcare provider, where the order of priority scores determines which entities (e.g., people, messaging reception services, or the like) are selected for a contact attempt.

In some embodiments, the prioritization heuristic may include instructions to independently update a priority score with respect to each label of a set of health condition labels. For example, a patient may be labeled with the health condition labels "scoliosis" and "psoriasis." In some embodiments, a prioritization heuristic may associate the condition "scoliosis" with a prioritization weight equal to "10" and the condition "psoriasis" with a prioritization weight equal to "1." The resource allocation system may then increase the priority score by "10" and "1," respectively, resulting in a priority score increase equal to "11." As an example, a prioritization heuristic may be represented by Equation 1, where j is an index value representing a patient identifier or other identifier associated with a patient record, N is the total number of health condition labels available, $P_j$ is the priority score for record j, $w_{ij}$ represents the prioritization weight associated with health condition label i for the record j, and $d_{ij}$ represents the presence of health condition label i for record j, where $d_{ij}$ may be 1 if the health condition label i is present and 0 otherwise:

$$P_j = \sum_{i=1}^{N} w_{ij} d_{ij} \qquad (1)$$

In some embodiments, the prioritization heuristic may include instructions to increase or decrease the magnitude of a change in a priority score when a plurality of health condition labels are associated with a patient or when specific sets of health condition labels are associated with a patient. For example, a prioritization heuristic may also include instructions to increase the priority score by 10 if a patient record includes the health condition label "dementia" and to increase the priority score by "20" if the patient record includes the health condition label "HIV." In some embodiments, the prioritization heuristic may also include instructions to increase the priority score by "30" if the patient record includes both the health condition labels "depression" and "HIV," resulting in a net increase equal to "60" to the priority score. In some embodiments, the use of specific sets of health condition labels may account for the co-morbidity of chronic illnesses or other negative long-term health conditions. As an example, a prioritization heuristic may be represented by Equation 2, which is based on Equation 1, where $d_{ij\text{-}chronic}$ represents a function that is equal to 1 if the health condition label i is present and also classified as a chronic health condition and 0 otherwise, and where M is a prioritization constant to add to a priority score for each additional chronic health condition associated with a patient after a first chronic health condition:

$$P_j = \sum_{i=1}^{N} w_{ij} d_{ij} + M\left(\sum_{i=1}^{N} d_{ij\text{-}chronic} - 1\right) \qquad (2)$$

In some embodiments, the priority score of a patient record may be determined based on a time value stored in the patient record. For example, a prioritization heuristic may include instructions to prioritize patients based on a most recent time of care for a criteria-selected health condition label. A time of care associated with a health condition may correspond with an event (e.g., a provider visit, a telehealth conference, or the like) that resulted in a patient being assigned the health condition. Alternatively, or in addition, a time of care associated with a health condition may correspond with an event that resulted in an update to a health metric associated with that health condition. For example, the health metric "eyesight" may be related to the health condition "glaucoma," and a time value that resulted in an update to the health score for "eyesight" may be explicitly set as associated with the health condition label "glaucoma."

In some embodiments, a resource allocation system may determine that a patient that had had a criteria-relevant checkup with a healthcare provider within a time threshold should have a lower priority score with respect to a patient that had not had a criteria-relevant checkup with any healthcare providers within the time threshold. For example, if a criteria-selected health condition label is "glaucoma," a prioritization heuristic may increase the priority score of a first patient if the first patient had not visited a doctor for eye-related issues within a time threshold equal to one year.

By taking time values associated with criteria-selected health conditions or other prioritization criteria into account when determining a priority score, a resource allocation system may allocate healthcare resources with far greater efficiency. Various heuristics may be used to take into account the complex interactions between time values, health conditions, or health scores, and may depend on a set of population health goals. As an example, a prioritization heuristic may be represented by Equation 3, which is based on Equation 2, where $\delta_{ic}$ represents a Kronecker delta function indicating if the health condition label i is a criteria-selected health condition label, H is a Heaviside function, $t_i$ is the most recent time value associated with the health condition label i, t is a current time, which can indicate that the expression "$(t_i-t)$" is an elapsed time, and $\Delta t_{thresh}$ is a time threshold:

$$P_j = \sum_{i=1}^{N} w_{ij} d_{ij} \delta_{ic} H((t_i - t) + \Delta t_{thresh}) + M\left(\sum_{i=1}^{N} \delta_{ij} - 1\right) \qquad (3)$$

As shown by Expression 3, the expression "$H((t_i-t)\Delta t_{thresh})$" may be a functional representation indicating an operation to determine whether the elapsed time satisfies the time threshold. If the elapsed time satisfies the time threshold, $H((t_i-t)+\Delta t_{thresh})$ may be equal to "1," whereas an elapsed time that does not satisfy the time threshold may result in the expression "$H((t_i-t)+\Delta t_{thresh})$" being equal to "0."

In some embodiments, the resource allocation system may determine a priority score based on a pattern detected from a plurality of health scores or health condition labels over time. For example, the resource allocation system may use a prioritization heuristic that includes a rule to detect a specified pattern over a set of health scores over time, where the specified pattern may include a monotonic increase in health scores over time, a monotonic decrease in health scores over time, an oscillating sequence, or the like. For example, the resource allocation system may determine a first pattern based on a sequence of three health scores "3.4%," "4.0%," and "6.5%," where each health score is associated with the health metric "A1C," and where each health score is associated with a different time value indicating a date on which the health score was obtained. In response to the detected pattern, the system may increase a corresponding priority score. In some embodiments, the amount by which a resource allocation system may change a priority score may be based on an absolute or relative amount of change between one or more health scores. For example, the resource allocation system may increase a priority score by "10" if the difference between two health scores over a time interval for a patient is 7% and may increase a priority score by "30" if the difference between the two health scores over a time interval is 9%.

In some embodiments, the resource allocation system may use a prioritization heuristic that includes quantitative distinctions in the way a health condition label obtained from one or more operations described for block 302 or block 304 and system-detected health conditions determined from block 330 changes or otherwise determines a priority score. For example, a health condition label named "leukemia" assigned by a healthcare provider and obtained using an operation described for block 302 may increase a priority score by "50." In contrast, a system-detected health condition label that is also named "leukemia" assigned by the resource allocation system using an operation described for block 330 may increase a priority score by "20." Alternatively, some embodiments may use a prioritization heuristic that does not make quantitative distinctions between the two types of health condition labels.

In some embodiments, the resource allocation system may use prioritization heuristics that include quantitative weights based on an expected health outcome that results from the use of a healthcare resource for a patient. A prioritization heuristic may change the prioritization score associated with a patient record by a predicted improvement weight based on a predicted health improvement. For example, a first patient that has a set of health scores associated with the health condition "pre-diabetes" may have a predicted health improvement weight equal to 40. A second patient that has health scores associated with the health condition "stage 4 terminal cancer" may have a predicted improvement weight equal to 5. In response, the prioritization heuristic may increase the priority score of the first patient by 40 and increase the priority score of the second patient by 5. Some embodiments may increase the total health of a population by changing priority scores based on predicted health improvements when performing operations to determine a priority score. Alternatively, or in addition, some embodiments may change a sequence of records based on predicted improvement weights or change the allocation of healthcare resources based on the predicted improvement weights.

In some embodiments, the resource allocation system may acquire a prioritization heuristic or prioritization parameters used by the prioritization heuristic from a persistent data store. For example, the resource allocation system may send a query to an API of a database that includes a set of prioritization heuristics and their corresponding prioritization weights, where the query includes a population size, a geographic size in which the population is distributed, the population density, and a prioritization criterion. In response, the database may provide a set of recommended prioritization heuristics. In addition, the database may provide descriptions or population health outcomes associated with the set of recommended prioritization heuristics to better decisions. In some embodiments, the resource allocation system may be scheduled to update one or more prioritization heuristics based on values obtained from the database. In some embodiments, the resource allocation system may receive instructions to update a prioritization heuristic based on a new set of prioritization parameters such as a set of prioritization weights. For example, an external data system may send a message to the resource allocation system that encodes instructions to change a prioritization weight from an initial value "10" to a new value "50." After authenticating the message, the resource allocation system may update the prioritization heuristic to use the new prioritization weight "50." In some embodiments, the new set of prioritization parameters may include a new set of prioritization weights, a new rule, instructions to delete a rule, new neural network weight values, or the like.

In some embodiments, the process 300 may include updating an ancillary record associated with the respective obtained record based on the priority score, as indicated by block 340. The ancillary record may include one or more values from the respective record and may also include additional values such as the priority score or the set of system-detected health condition labels. For example, the ancillary record may include a patient name and a health condition label stored in the respective obtained record of the patient. In addition, or alternatively, the respective obtained record may include one or more values not stored in the ancillary record. For example, the respective obtained record may include a quantitative blood glucose measurement, while its associated ancillary record may not include any quantitative blood glucose measurement. Furthermore, calculations to determine the priority score may be stored in the ancillary record or transmitted to a display device. By storing the calculations used to determine the priority score, the resource allocation system may be more transparent, interpetable, and explainable, which may increase the accuracy of learning systems used by the resource allocation system and enhance the ease of integration with health outcome optimization systems.

In some embodiments, the process 300 may include determining whether additional records from the population of records is to be processed, as indicated by block 342. In some embodiments, every one of the records from the population of records are to be processed. Alternatively, some embodiments may include one or more search filters or stopping condition to stop operations to prioritize one or more records in the population of records. Some embodiments may sequentially loop through each record of the population of records. Some embodiments may include using a computing system capable of parallel processing and apply one or more operations described this application in parallel. If additional records are to be processed operations of the process 300 may return to block 320. Otherwise, operations of the process 300 may proceed to block 350.

In some embodiments, the process 300 may include re-encrypting one or more records of the population of records using the encryption key, as indicated by block 350. In some embodiments, the population of records may be encrypted using the same encryption key as the encryption key used to decrypt the record. The encryption method used may be associated with the decryption method used as described for block 308. For example, if the records were decrypted using an RSA decryption method, the records may be re-encrypted using an RSA encryption method.

While the above example describes encrypting and decrypting multiple records at a time, some embodiments may iteratively decrypt and re-encrypt records individually. For example, the process 300 may include decrypting the first record during an operation described for block 330 and encrypting the first record during an operation described for block 340. In some embodiments, a plurality of encryption keys may be used, where each record may require its own encryption key. Alternatively, or in addition, subsets of records in the population of records may be decrypted the encrypted with their own encryption key. Alternatively, while the above process includes re-encrypting one or more records, some embodiments may proceed without encrypting any records of the population of records. In some embodiments, the process 300 may include deleting health scores, health condition labels, or other information associated with a patient that is not necessary for a resource allocation operation. For example, after assigning a priority score, a resource allocation system may delete a local version of the population of records and use a set of ancillary records storing only a patient identifier, patient name, patient contact information, primary care provider identifier, relevant condition, priority score, or most recent contact event. In some embodiments, data storage and data transfer may occur using ancillary records instead of an original population of records for data related to patient health or patient identity. The storage and use of data in the set of ancillary records may increase the efficiency and security of a resource allocation system by reducing the computational resources needed to retrieve data from a larger dataset such as a full population of records.

In some embodiments, the process 300 may include determining a set of correlation values or other population statistics based on the priority scores, as indicated by block 352. A correlation value may be any type of value that indicates or measures a correlation between two or more variables. For example, some embodiments may determine a correlation value indicating the correlation between priority scores and a health condition label such as "hypochondria."

In some embodiments, a correlation value or other population statistic may be determined based on outcome scores. An outcome score may be determined using historical data associated with a population of records. For example, some embodiments may determine outcome scores for a population of records based on the health changes measured by health scores and health condition labels one year after the implementation of a prioritization heuristic. Alternatively, or in addition, outcome scores for a prioritization heuristic may be determined using one or more applications to simulate a response to the implementation of a population health plan using the prioritization heuristic.

In some embodiments, a population statistic may be based on one or more demographic labels associated with a population. A demographic label may indicate a demographic value as an age, a home location, an ethnicity, an occupation, a related set of activities (e.g., people who exercise, people who eat a particular type of food, or the like). For example, some embodiments may be used to determine a mean average priority score for all patients between the ages of 50 to 70. In some embodiments, the analysis system may search through the population of records to determine a demographic combination based on a set of demographic labels associated with a plurality of the population of records. For example, a first demographic label of the population of records may include an age category such as "18 to 25," and a second demographic label the population of records may include an occupation such as "farm laborer." The analysis system may then compare a correlation value based on the number of records associated with the label "diabetes" and the first demographic label, a second correlation value based on the number of records associated with the label "diabetes" and the second demographic label, and a third correlation value based on the number of records associated with a label "diabetes" and a demographic combination that includes the first demographic label and the second demographic label. The system may then use the three correlation values to determine if there is a co-morbidity effect or other possible effects for individuals that have both demographic labels.

While the above examples include operations to determine a correlation value, other embodiments may determine one or more other population statistics. Other population statistics may include a measure of central tendency such as a mean average, a median average, a mode, or the like. For example, some embodiments may determine a mean average priority score and a median priority score. Alternatively, or in addition, a population statistic may include a measure of variation such as a standard deviation, a variance, a confidence interval, or the like. Alternatively, or in addition, a population statistic may include a measure of a distribution tail shape such as a kurtosis measurement or a skewness measurement.

In some embodiments, the resource allocation system may determine whether the correlation value or other population statistic satisfies a reporting threshold. In response to the correlation value satisfying the reporting threshold, the analysis system may display a message indicating that the correlation value satisfies the reporting threshold or send the message to an API. For example, in response to a mean average priority score for a population exceeding a reporting threshold, some embodiments may send an alert to an API of a server.

In some embodiments, the process 300 may include determining a sequence of records by sorting the plurality of priority scores, as indicated by block 354. The resource allocation system may sort the set of records into a sequence of records based on their corresponding priority scores. The plurality of priority scores may be sorted using various sorting algorithms. For example, the resource allocation system may use a Quicksort algorithm to sort the set of 60,000 priority scores. Various other sorting algorithms may be used, such as variations of the merge sort algorithm, variations of the heap sort algorithm, variations of the Quicksort algorithm, variations of the shells sort algorithm, or the like. During sorting, additional filters may be applied to remove one or more records from consideration for display or transmittal. In some embodiments, the resource allocation system may apply filters based on one or more of the set of prioritization criteria. For example, some embodiments may include the criteria-selected health condition label "diabetes," and, in response, the resource allocation system may discard or otherwise prevent the display or transmission of data from patient records not associated with the health condition label "diabetes."

In some embodiments, the resource allocation system may predict a set of anticipated appointment durations associated with the sequence of patients. In some embodiments, the resource allocation system may then match the patients of the sequence of records with their associated healthcare resource(s) or otherwise obtain the associated healthcare resource(s) for the patients using algorithms designed to address a bin-packing problem. For example, a sequence of ten patients may be predicted to require appointment durations ranging between 10 minutes to 120 minutes, where each of the ten patients are to be seen by one of three healthcare providers. A resource allocation system may then propose a set of schedules matching each patient with a time slot of the provider's utilization schedule using one or more types of packing algorithms, such as a first-fit algorithm, an MTP algorithm, Bin Completion algorithm, or the like.

In some embodiments, the process 300 may include obtaining a set of utilization schedules of a set of healthcare resources based on a set of resource identifiers associated with the sequence of records, as indicated by block 356. In some embodiments, a resource allocation system may send a healthcare resource identifier associated with the sequence of records to a scheduling system that includes a set of utilization schedules. Example utilization schedules of healthcare resources may include the time schedule of a primary care provider, travel times of a mobile clinic, a use schedule of an MRI machine, or the like. In some embodiments, the resource allocation system may obtain the utilization schedule of the corresponding resource based on the healthcare resource identifier by referring to a data store that is part of the resource allocation system. Alternatively, or in addition, the resource allocation system may send a request that includes a resource identifier to an API of a scheduling application, where the request causes the scheduling application to respond with a utilization schedule of the healthcare resource identified by the resource identifier.

In some embodiments, a healthcare resource may be matched with or otherwise obtained for one or more patients based on the sequence of records and factors associated with the availability of a healthcare resource, such as an anticipated available time slot, geographic proximity, or the like. For example, some embodiments may partition a sequence of records into multiple sub-sequences of records based on their respective required healthcare resource(s). Some embodiments may then search through a set of available healthcare resources, sort them by their available time slots, and assign each of the ranked patients into their needed healthcare resources based on the available time slots and the resource identifiers or associated their respective sub-sequence of records. Some embodiments may implement a set of bin-packing algorithms to increase the number of high-priority patients utilizing the available healthcare resources of a region based on their respective sub-sequences. By using an algorithmic approach to match healthcare resources with patients based on their respective priority scores or availability, some embodiments may increase the efficiency of healthcare resource deployment in an area and increase the long-term health of a population in the area.

In some embodiments, the process 300 may include sending a selected set of identifiers or other information associated with the selected set of identifiers from the sequence of records to a display device or an API, as indicated by block 358. Identifiers of a sequence of records may include record-specific identifiers such as record index values, patient-specific identifiers, or the like. In some embodiments, identifiers may be sent by sending the entirety of a corresponding record from the population of records or the corresponding ancillary record. Alternatively, or in addition, identifiers may be sent in isolation or in association with other values of their corresponding record, where the entirety of the record is not sent. For example, a patient-specific identifier may be sent in a message along with the patient's name, patient's primary care provider, and a set of contact values corresponding to the patient, where a contact value may be a value usable for contacting the patient. Contact values may include a postal address, a phone number, an email, an application account name, a social media account name, a messaging software account name, or the like. In addition, some embodiments may send an identifier or associated values from each of the records in the sequence of records. Alternatively, some embodiments may send values (e.g., numbers, categories, text, or the like) from a subset of the sequence of records, such as the values from records associated with the N greatest priority scores or the values from records associated with the N least priority scores, where N may be a constant integer. By listing patients in a prioritized sequence for display, the resource allocation system allows a user to prioritize patients based on which patients are likely to most benefit from a contact attempt. While the above discloses an embodiment that provides this advantage, not all embodiments provide the advantage, and some embodiments may lack the advantage or in view of trade-offs or other advantages. Furthermore, some embodiments to schedule or otherwise obtain healthcare resources for patients may use methods described in the patent application U.S. Ser. No. 16/222,797, which is hereby incorporated by reference.

In some embodiments, sending data to a display device may include sending data encoding a set of contact values usable for contacting a patient via an electronic communication system. In some embodiments, the use of a text-based communication system sent to a mobile device may enable communication that may otherwise be unseen or ignored by patients. For example, some embodiments may send an account name associated with an account of the patient on a social media platform or messaging platform to a display device. A user may interact with a user interface element on the display device to open a messaging client that allows the user to contact the patient via the patient's social media or messaging account. Alternatively, or in addition, a user interface displayed on the display device may include one or more user interface elements to contact a patient by sending a text message to the patient's phone via SMS texting.

In some embodiments, the display device may include additional information determined from a set of previous contact attempt times with a patient. For example, a user interface may display a patient's name, a patient's phone number, a set of previous contact attempt times, and a set of values indicating successes or failures associated with each corresponding contact attempt from the set of previous contact attempt times. In some embodiments, the resource allocation system may suggest a future contact time during which contact with the patient is likely to be successful and send this future contact time to the display device to be viewed by a user.

In some embodiments, the user interface element may include a visual marker indicating that a patient had or had not been contacted within a threshold period of time. Various visual markers may be used, such as an icon, a text color, a background color, a transparency, or the like. For example, a user interface may include a list of patients, where a first subset of the list of patients have a checkmark or green background to indicate that they have been contacted within a threshold period of time, and a second subset of the list of patients have a red background to indicate that they have not been contacted within the threshold period of time.

In some embodiments, the resource allocation system may include or otherwise be integrated with a scheduling system and may display the availability of other healthcare resources associated with a list of displayed patients. For example, some embodiments may also include operations to send a set of utilization schedules to a display device for display. In some embodiments, a user interface element displayed on the display device may then display the utilization schedule in conjunction with a list of patient identifiers, and may dynamically change in response to the list of patient identifiers. For example, after a user taps on a patient in a patient list displayed in a user interface, the user interface may show a utilization schedule of a primary care provider listed as being responsible for the patient.

In some embodiments, the process 300 may include updating one or more records based on a response provided by a user or a response received at an API, as indicated by block 370. In some embodiments, the resource allocation system may receive feedback from a user or a computer-implemented program. This feedback may be used to update one or more records of the population of records or update other data such as an ancillary record associated with the one or records of a population of records. For example, the resource allocation system may receive a new time value indicating that a patient had visited a healthcare provider. In response, the resource allocation system may update its set of time values to include the new time value indicating the time of the visit associated with the patient, which may then reduce the priority score corresponding to the patient.

In some embodiments, updates to the priority values may also be used to update a prioritization heuristic. For example, a user may interact with a set of user interface elements to reorder a list of patients, and, in response, the resource allocation system may receive the message including in the ordered list of patients. The resource allocation system may then update one or more prioritization weights or other prioritization parameters to increase or decrease the priority scores assigned to one or more records to match the reordered list of patients. In some embodiments, one or more values of a set of responses may be collected and used to train a neural network operating under a reinforcement learning architecture. For example, a neural network used to determine a system-detected health condition may be updated based on a user response indicating that the system-detected health condition has been confirmed by a healthcare provider.

Computer System

Figure 4:
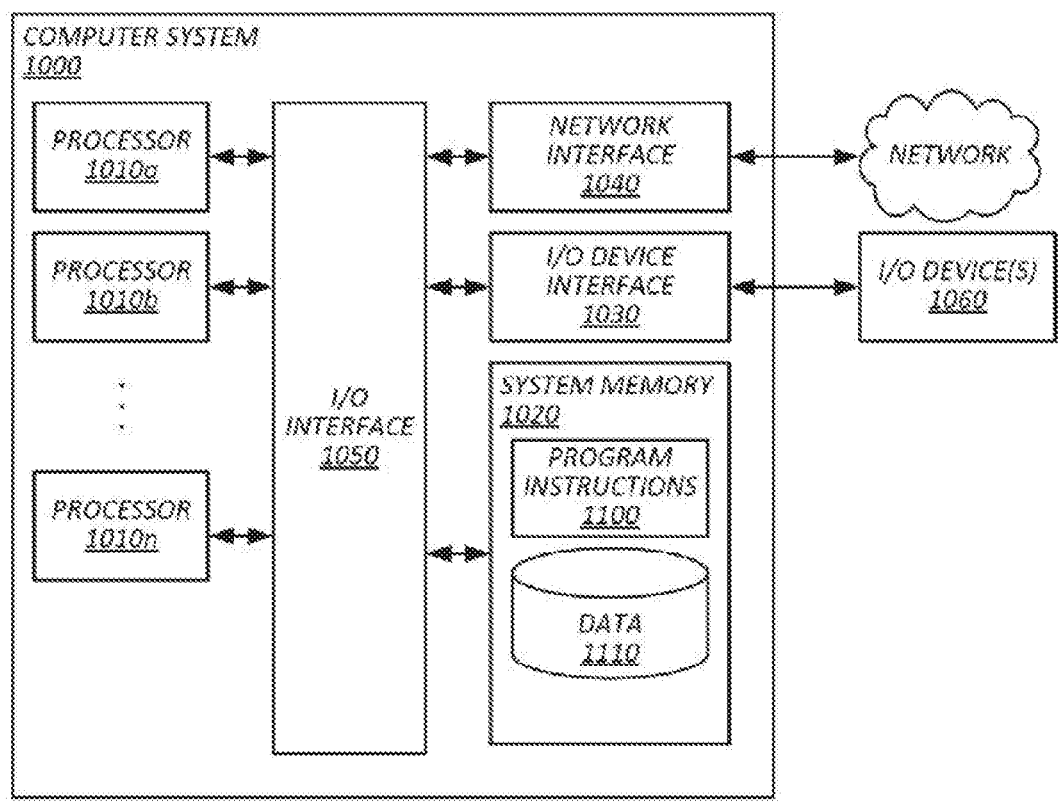
FIG. 4 shows an exemplary computing system by which the present techniques may be implemented in accordance with some embodiments.

FIG. 4 shows an exemplary computing system 1000 by which the present techniques may be implemented in accordance with some embodiments. Various portions of systems and methods described herein, may include or be executed on one or more computer systems similar to computing system 1000. Further, processes and modules described herein may be executed by one or more processing systems similar to that of computing system 1000.

Computing system 1000 may include one or more processors (e.g., processors 1010a-1010n) coupled to system memory 1020, an input/output I/O device interface 1030, and a network interface 1040 via an input/output (I/O) interface 1050. A processor may include a single processor or a plurality of processors (e.g., distributed processors). A processor may be any suitable processor capable of executing or otherwise performing instructions. A processor may include a central processing unit (CPU) that carries out program instructions to perform the arithmetical, logical, and input/output operations of computing system 1000. A processor may execute code (e.g., processor firmware, a protocol stack, a database management system, an operating system, or a combination thereof) that creates an execution environment for program instructions. A processor may include a programmable processor. A processor may include general or special purpose microprocessors. A processor may receive instructions and data from a memory (e.g., system memory 1020). Computing system 1000 may be a uni-processor system including one processor (e.g., processor 1010a), or a multi-processor system including any number of suitable processors (e.g., 1010a-1010n). Multiple processors may be employed to provide for parallel or sequential execution of one or more portions of the techniques described herein. Processes, such as logic flows, described herein may be performed by one or more programmable processors executing one or more computer programs to perform functions by operating on input data and generating corresponding output. Processes described herein may be performed by, and apparatus can also be implemented as, special purpose logic circuitry, e.g., a vision processing unit (VPU), a neuromorphic complementary metal-oxide-semiconductor (CMOS) chip, an FPGA (field programmable gate array), a PGA (programmable gate array), or an ASIC (application specific integrated circuit) such as a tensor processing unit (TPU). Computing system 1000 may include a plurality of computing devices (e.g., distributed computer systems) to implement various processing functions.

I/O device interface 1030 may provide an interface for connection of one or more I/O devices 1060 to computing system 1000. I/O devices may include devices that receive input (e.g., from a user) or output information (e.g., to a user). I/O devices 1060 may include, for example, graphical user interface presented on displays (e.g., a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, or the like. I/O devices 1060 may be connected to computing system 1000 through a wired or wireless connection. I/O devices 1060 may be connected to computing system 1000 from a remote location. I/O devices 1060 located on remote computer system, for example, may be connected to computing system 1000 via a network and network interface 1040.

Network interface 1040 may include a network adapter that provides for connection of computing system 1000 to a network. Network interface may 1040 may facilitate data exchange between computing system 1000 and other devices connected to the network. Network interface 1040 may support wired or wireless communication. The network may include an electronic communication network, such as the Internet, a local area network (LAN), a wide area network (WAN), a cellular communications network, or the like.

System memory 1020 may be configured to store program instructions 1100 or data 1110. Program instructions 1100 may be executable by a processor (e.g., one or more of processors 1010a-1010n) to implement one or more embodiments of the present techniques. Instructions 1100 may include modules of computer program instructions for implementing one or more techniques described herein with regard to various processing modules. Program instructions may include a computer program (which in certain forms is known as a program, software, software application, script, or code). A computer program may be written in a programming language, including compiled or interpreted languages, or declarative or procedural languages. A computer program may include a unit suitable for use in a computing environment, including as a stand-alone program, a module, a component, or a subroutine. A computer program may or may not correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one or more computer processors located locally at one site or distributed across multiple remote sites and interconnected by a communication network.

System memory 1020 may include a tangible program carrier having program instructions stored thereon. A tangible program carrier may include a non-transitory computer readable storage medium. A non-transitory, computer-readable storage medium may include a machine readable storage device, a machine readable storage substrate, a memory device, or any combination thereof. Non-transitory computer readable storage medium may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM or DVD-ROM, hard-drives), or the like. System memory 1020 may include a non-transitory computer readable storage medium that may have program instructions stored thereon that are executable by a computer processor (e.g., one or more of processors 1010a-1010n) to cause the subject matter and the functional operations described herein. A memory (e.g., system memory 1020) may include a single memory device or a plurality of memory devices (e.g., distributed memory devices). Instructions or other program code to provide the functionality described herein may be stored on a tangible, non-transitory computer readable media. In some cases, the entire set of instructions may be stored concurrently on the media, or in some cases, different parts of the instructions may be stored on the same media at different times.

I/O interface 1050 may be configured to coordinate I/O traffic between processors 1010a-1010n, system memory 1020, network interface 1040, I/O devices 1060, or other peripheral devices. I/O interface 1050 may perform protocol, timing, or other data transformations to convert data signals from one component (e.g., system memory 1020) into a format suitable for use by another component (e.g., processors 1010a-1010n). I/O interface 1050 may include support for devices attached through various types of peripheral buses, such as a variant of the Peripheral Component Interconnect (PCI) bus standard or the Universal Serial Bus (USB) standard.

Embodiments of the techniques described herein may be implemented using a single instance of computing system 1000 or multiple computing systems 1000 configured to host different portions or instances of embodiments. Multiple computing systems 1000 may provide for parallel or sequential processing/execution of one or more portions of the techniques described herein.

Those skilled in the art will appreciate that computing system 1000 is merely illustrative and is not intended to limit the scope of the techniques described herein. Computing system 1000 may include any combination of mobile computing devices or software that may perform or otherwise provide for the performance of the techniques described herein. For example, computing system 1000 may include or be a combination of a cloud-computing system, a data center, a server rack, a server, a virtual server, a desktop computer, a laptop computer, a tablet computer, a server device, a client device, a mobile telephone, a personal digital assistant (PDA), a mobile audio or video player, a game console, a vehicle-mounted computer, or a Global Positioning System (GPS), or the like. Computing system 1000 may also be connected to other devices that are not illustrated, or may operate as a stand-alone system. In addition, the functionality provided by the illustrated components may, in some embodiments, be combined in fewer components or distributed in additional components. Similarly, in some embodiments, the functionality of some of the illustrated components may not be provided or other additional functionality may be available.

Those skilled in the art will also appreciate that while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 1000 may be transmitted to computer system 1000 via transmission media or signals such as electrical, electromagnetic, or digital signals, conveyed via a communication medium such as a network or a wireless link. Various embodiments may further include receiving, sending, or storing instructions or data implemented in accordance with the foregoing description upon a computer-accessible medium. Accordingly, the present techniques may be practiced with other computer system configurations.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, notwithstanding use of the singular term "medium," the instructions may be distributed on different storage devices associated with different computing devices, for instance, with each computing device having a different subset of the instructions, an implementation consistent with usage of the singular term "medium" herein. In some cases, third party content delivery networks may host some or all of the information conveyed over networks, in which case, to the extent information (e.g., content) is said to be supplied or otherwise provided, the information may be provided by sending instructions to retrieve that information from a content delivery network.

The reader should appreciate that the present application describes several independently useful techniques. Rather than separating those techniques into multiple isolated patent applications, applicants have grouped these techniques into a single document because their related subject matter lends itself to economies in the application process. But the distinct advantages and aspects of such techniques should not be conflated. In some cases, embodiments address all of the deficiencies noted herein, but it should be understood that the techniques are independently useful, and some embodiments address only a subset of such problems or offer other, unmentioned benefits that will be apparent to those of skill in the art reviewing the present disclosure. Due to costs constraints, some techniques disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such techniques or all aspects of such techniques.

It should be understood that the description and the drawings are not intended to limit the present techniques to the particular form disclosed, but to the contrary, the intention is to cover all modifications, equivalents, and alternatives falling within the spirit and scope of the present techniques as defined by the appended claims. Further modifications and alternative embodiments of various aspects of the techniques will be apparent to those skilled in the art in view of this description. Accordingly, this description and the drawings are to be construed as illustrative only and are for the purpose of teaching those skilled in the art the general manner of carrying out the present techniques. It is to be understood that the forms of the present techniques shown and described herein are to be taken as examples of embodiments. Elements and materials may be substituted for those illustrated and described herein, parts and processes may be reversed or omitted, and certain features of the present techniques may be utilized independently, all as would be apparent to one skilled in the art after having the benefit of this description of the present techniques. Changes may be made in the elements described herein without departing from the spirit and scope of the present techniques as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Similarly, reference to "a computer system" performing step A and "the computer system" performing step B can include the same computing device within the computer system performing both steps or different computing devices within the computer system performing steps A and B. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device. Features described with reference to geometric constructs, like "parallel," "perpendicular/orthogonal," "square", "cylindrical," and the like, should be construed as encompassing items that substantially embody the properties of the geometric construct, e.g., reference to "parallel" surfaces encompasses substantially parallel surfaces. The permitted range of deviation from Platonic ideals of these geometric constructs is to be determined with reference to ranges in the specification, and where such ranges are not stated, with reference to industry norms in the field of use, and where such ranges are not defined, with reference to industry norms in the field of manufacturing of the designated feature, and where such ranges are not defined, features substantially embodying a geometric construct should be construed to include those features within 15% of the defining attributes of that geometric construct. The terms "first", "second", "third," "given" and so on, if used in the claims, are used to distinguish or otherwise identify, and not to show a sequential or numerical limitation. As is the case in ordinary usage in the field, data structures and formats described with reference to uses salient to a human need not be presented in a human-intelligible format to constitute the described data structure or format, e.g., text need not be rendered or even encoded in Unicode or ASCII to constitute text; images, maps, and data-visualizations need not be displayed or decoded to constitute images, maps, and data-visualizations, respectively; speech, music, and other audio need not be emitted through a speaker or decoded to constitute speech, music, or other audio, respectively. Computer implemented instructions, commands, and the like are not limited to executable code and can be implemented in the form of data that causes functionality to be invoked, e.g., in the form of arguments of a function or API call. To the extent bespoke noun phrases are used in the claims and lack a self-evident construction, the definition of such phrases may be recited in the claim itself, in which case, the use of such bespoke noun phrases should not be taken as invitation to impart additional limitations by looking to the specification or extrinsic evidence.

In this patent, to the extent any U.S. patents, U.S. patent applications, or other materials (e.g., articles) have been incorporated by reference, the text of such materials is only incorporated by reference to the extent that no conflict exists between such material and the statements and drawings set forth herein. In the event of such conflict, the text of the present document governs, and terms in this document should not be given a narrower reading in virtue of the way in which those terms are used in other materials incorporated by reference.

The present techniques will be better understood with reference to the following enumerated embodiments:

1. A tangible, non-transitory, machine-readable medium storing instructions that when executed by one or more processors effectuate operations comprising: obtaining, with the computing system, a population of patient records, wherein: each respective record of the population of patient records comprises a respective set of time values, a respective set of health scores associated with a respective patient identifier, and a respective healthcare resource identifier, and each time value of the respective set of time values indicates an event occurrence time, wherein the event occurrence time is associated with an update to the respective set of health scores; assigning, with the computing system, a plurality of priority scores to the population of patient records using a prioritization heuristic based on a prioritization criterion, wherein the population of patient records comprises a first patient record and a second patient record, and wherein using the prioritization heuristic comprises: determining a first elapsed time based on a first time value of the first patient record, wherein the first patient record comprises a first health score, and wherein the first time value and the first health score are associated with the prioritization criterion; determining a first priority score associated with the first patient record based on the first elapsed time and the first health score; determining a second priority score associated with the second patient record based on a second time value and a second health score, wherein the second patient record comprises the second time value and the second health score, and wherein the second time value and the second health score are associated with the prioritization criterion; sorting, with the computing system, the plurality of priority scores into a sequence of priority scores to determine a sequence of records from the population of patient records; and obtaining a utilization schedule of a healthcare resource based on a resource identifier, wherein the resource identifier is determined based on a record selected from the sequence of records.

2. The medium of embodiment 1, wherein determining the first priority score comprises determining whether the first elapsed time satisfies a time threshold, and wherein satisfying the time threshold with the first elapsed time causes a change in the first priority score.

3. The medium of any one of embodiments 1-2, the operations further comprising: determining a system-detected health condition label based on the first health score and a sequence of text stored in the first patient record using a rule; and associating the system-detected health condition label with the first patient record.

4. The medium of any one of embodiments 1-3, the operations further comprising: determining a first health condition label based on a set of health scores of the first patient record, wherein the first health condition label is not yet associated with the first patient record; and associating the first health condition label with the first patient record, wherein the first health condition label is indicated as a system-detected health condition label.

5. The medium of any one of embodiments 1-4, wherein obtaining the population of patient records comprises: determining a data format of the first patient record; determining whether the data format satisfies a set of data format criteria; and in response to a determination that the data format does not satisfy the set of data format criteria, generate a version of the first patient record based on a format transformation heuristic, wherein the format transformation heuristic comprises a data size reduction operation.

6. The medium of any one of embodiments 1-5, wherein the first patient record identifies a first person, and wherein the operations further comprise displaying values associated with the sequence of records in a user interface, wherein the values comprise a name of the first person and a contact value of the first person, and wherein the user interface comprises a user interface element to indicate whether the first person had already been contacted within a threshold period of time.

7. The medium of any one of embodiments 1-6, the operations further comprising: searching through the population of patient records to determine a demographic combination based on a set of demographic labels; determining a correlation value based on the demographic combination and a health condition label; determining whether the correlation value satisfies a reporting threshold; and displaying a message indicating that the correlation value satisfies the reporting threshold.

8. The medium of any one of embodiments 1-7, the operations further comprising determining a future contact time for the first patient record based on a set of previous contact attempt times associated with the first patient record, wherein each attempt time of the set of previous contact attempt times is associated with an indicator that indicates whether a corresponding contact attempt was successful or failed.

9. The medium of any one of embodiments 1-8, the operations further comprising: receiving a message comprising a new set of prioritization parameters at an application program interface; authenticating the message; and updating the prioritization heuristic based on the new set of prioritization parameters.

10. The medium of any one of embodiments 1-9, wherein the operations further comprising determining a resource allocation associated with the first patient record, wherein the resource allocation comprises one of a time interval, an identifier associated with a piece of equipment, a healthcare provider, or a healthcare facility.

11. The medium of any one of embodiments 1-10, the operations further comprising sending a set of patient identifiers of the sequence of records to an application program interface.

12. The medium of any one of embodiments 1-11, wherein the first patient record identifies a first person, and wherein the operations further comprise: updating the first patient record with a new time value to indicate that the first person had visited a healthcare provider; and changing the first priority score based on the new time value.

13. The medium of any one of embodiments 1-12, wherein the first patient record identifies a first person, and wherein the operations further comprise: determining a contact identifier associated with the first person, wherein the contact identifier is associated with a signature key; and transmitting a message to an application program interface (API) of a text-based communication system, wherein the message comprises the contact identifier and the signature key.

14. The medium of any one of embodiments 1-13, wherein obtaining the population of patient records comprises obtaining the population of patient records from a first data store, and wherein the operations further comprises: sending a request an application program interface enabling communication with a second data store to obtain a response to the request; and updating the population of patient records based on the response.

15. The medium of any one of embodiments 1-14, wherein the first patient record is initially encrypted, and wherein the operations further comprising: obtaining an encryption key; decrypting the first patient record using the encryption key; and encrypting the first patient record after determining the first priority score using the encryption key.

16. The medium of any one of embodiments 1-15, wherein determining the first priority score comprises determining the first priority score based on a plurality of health scores, wherein each of the plurality of health scores is associated with a different time value in a set of time values of the first patient record.

17. The medium of any one of embodiments 1-16, the operations further comprising: receiving a message at an application program interface, wherein the message comprises a sensor measurement; updating a first set of health scores of the first patient record based on the sensor measurement; and updating the first priority score based on the first set of health scores.

18. The medium of any one of embodiments 1-17, wherein obtaining the population of patient records comprises labeling the first patient record with a plurality of system-detected health condition labels based on a set of health scores of the first patient record.

19. The medium of any one of embodiments 1-18, the operations comprising increasing the first priority score in response to a determination that the first patient record is associated with a plurality of health condition labels.

20. A method, comprising: the operations of any one of embodiments 1-19.

21. A system, comprising: one or more processors; and memory storing instructions that when executed by the processors cause the processors to effectuate operations comprising: the operations of any one of embodiments 1-19.

What is claimed is:

1. A non-transitory, machine-readable medium storing instructions that, when executed by a computing system, effectuate operations comprising:
   obtaining, with the computing system, a population of patient records, wherein a count of the population of patient records is greater than or equal to 10,000 records, and wherein:
      each respective record of the population of patient records comprises a respective set of time values, a respective set of health scores associated with a respective patient identifier, and a respective healthcare resource identifier, and
      each time value of the respective set of time values indicates an event occurrence time, wherein the event occurrence time is associated with an update to the respective set of health scores;
   assigning, with the computing system, a plurality of priority scores to the population of patient records using a prioritization heuristic based on a prioritization criterion, wherein the population of patient records comprises a first patient record and a second patient record, and wherein using the prioritization heuristic comprises:
      determining a first elapsed time based on a first time value of the first patient record, wherein the first patient record comprises a first health score, and wherein the first time value and the first health score are associated with the prioritization criterion;
      determining a first priority score associated with the first patient record based on the first elapsed time and the first health score, wherein the plurality of priority scores comprises the first priority score; and
      determining a second priority score associated with the second patient record based on a second time value and a second health score, wherein the second patient record comprises the second time value and the second health score, and wherein the second time value and the second health score are associated with the prioritization criterion, and wherein the plurality of priority scores comprises the second priority score;
   sorting, with the computing system, the plurality of priority scores into a sequence of priority scores to determine a sequence of records from the population of patient records, wherein the first priority score is lower in the sequence of priority scores than the second priority score;
   obtaining, with the computing system, a utilization schedule of a healthcare resource based on a resource identifier, wherein the resource identifier is determined based on a record selected from the sequence of records; and
   displaying, with the computing system, values associated with the sequence of records in a user interface, wherein:
      the first patient record identifies a first person,
      the values comprise a name of the first person and a contact value of the first person,
      the user interface comprises a first user interface element to indicate whether the first person had already been contacted within a threshold period of time,
      the user interface comprises a second user interface element that, when interacted with, causes the user interface to dynamically populate the utilization schedule,
      the utilization schedule is displayed concurrently with the contact value of the first person on a same screen of the user interface, and
      interaction with an element of the utilization schedule causes the update of scheduling data stored in an external application via an application program interface.

2. The medium of claim 1, wherein determining the first priority score comprises determining whether the first elapsed time satisfies a time threshold, and wherein satisfying the time threshold with the first elapsed time causes a change in the first priority score.

3. The medium of claim 1, the operations further comprising:
   determining a system-detected health condition label based on the first health score and a sequence of text stored in the first patient record using a rule; and
   associating the system-detected health condition label with the first patient record.

4. The medium of claim 1, the operations further comprising:
   determining a first health condition label based on a set of health scores of the first patient record, wherein the first health condition label is not yet associated with the first patient record; and
   associating the first health condition label with the first patient record, wherein the first health condition label is indicated as a system-detected health condition label.

5. The medium of claim 1, wherein obtaining the population of patient records comprises:
   determining a data format of the first patient record;
   determining whether the data format satisfies a set of data format criteria; and
   in response to a determination that the data format does not satisfy the set of data format criteria, generating a version of the first patient record based on a format transformation heuristic, wherein the format transformation heuristic comprises a data size reduction operation.

6. The medium of claim 1, the operations further comprising:
   searching through the population of patient records to determine a demographic combination based on a set of demographic labels, wherein the demographic combination comprises a first set of records labeled with a first label of the set of demographic labels and a second set of records labeled with a second label of the set of demographic labels;
determining a correlation value based on the demographic combination and a health condition label based on a number of records in the demographic combination having the health condition label;
determining whether the correlation value satisfies a reporting threshold; and
displaying a message indicating that the correlation value satisfies the reporting threshold.

7. The medium of claim 1, the operations further comprising determining a future contact time for the first patient record based on a set of previous contact attempt times associated with the first patient record, wherein each attempt time of the set of previous contact attempt times is associated with an indicator that indicates whether a corresponding contact attempt was successful or failed.

8. The medium of claim 1, the operations further comprising:
receiving a message comprising a new set of prioritization parameters at an application program interface;
authenticating the message; and
updating the prioritization heuristic based on the new set of prioritization parameters.

9. The medium of claim 1, wherein the operations further comprising determining a resource allocation associated with the first patient record, wherein the resource allocation comprises one of a time interval, an identifier associated with a piece of equipment, a healthcare provider, or a healthcare facility.

10. The medium of claim 1, the operations further comprising sending a set of patient identifiers of the sequence of records to an application program interface.

11. The medium of claim 1, wherein the first patient record identifies a first person, and wherein the operations further comprise:
updating the first patient record with a new time value to indicate that the first person had visited a healthcare provider; and
changing the first priority score based on the new time value.

12. The medium of claim 1, wherein the first patient record identifies a first person, and wherein the operations further comprise:
determining a contact identifier associated with the first person, wherein the contact identifier is associated with a signature key; and
transmitting a message to an application program interface (API) of a text-based communication system, wherein the message comprises the contact identifier and the signature key.

13. The medium of claim 1, wherein obtaining the population of patient records comprises obtaining the population of patient records from a first data store, and wherein the operations further comprises:
sending a request an application program interface enabling communication with a second data store to obtain a response to the request; and
updating the population of patient records based on the response.

14. The medium of claim 1, wherein the first patient record is initially encrypted, and wherein the operations further comprising:
obtaining an encryption key;
decrypting the first patient record using the encryption key; and
encrypting the first patient record after determining the first priority score using the encryption key.

15. The medium of claim 1, wherein determining the first priority score comprises determining the first priority score based on a plurality of health scores, wherein each of the plurality of health scores is associated with a different time value in a set of time values of the first patient record.

16. The medium of claim 1, the operations further comprising:
receiving a message at an application program interface, wherein the message comprises a sensor measurement of a biometric sensor and a signature value;
verifying the message based on the signature value;
updating the first health score of the first patient record based on the sensor measurement; and
updating the first priority score based on the first set of health scores.

17. The medium of claim 1, wherein obtaining the population of patient records comprises labeling the first patient record with a plurality of system-detected health condition labels based on a set of health scores of the first patient record.

18. The medium of claim 1, the operations comprising increasing the first priority score in response to a determination that the first patient record is associated with a plurality of health condition labels.

19. The medium of claim 1,
wherein obtaining the population of patient records comprises:
obtaining a first version of the first patient record;
determining a data format of the first patient record;
determining whether the data format satisfies a set of data format criteria; and
in response to a determination that the data format does not satisfy the set of data format criteria, generating a second version of the first patient record based on a format transformation heuristic, the format transformation heuristic comprising:
approximating a first numeric value of the first version of the first patient record into a second numeric value, wherein the second numeric value has fewer digits than the first numeric value; and
storing the second numeric value in the second version of the first patient record.

20. The medium of claim 1, the operations further comprising:
searching through the population of patient records to determine a demographic combination based on a set of demographic labels, wherein the demographic combination comprises a first set of records labeled with a first label of the set of demographic labels and a second set of records labeled with a second label of the set of demographic labels;
determining a correlation value based on the demographic combination and a health condition label based on a number of records in the demographic combination having the health condition label;
determining whether the correlation value satisfies a reporting threshold;
displaying a message indicating that the correlation value satisfies the reporting threshold;
wherein obtaining the population of patient records comprises:
obtaining a first version of the first patient record;
determining a data format of the first patient record;
determining whether the data format satisfies a set of data format criteria; and in response to a determination that the data format does not satisfy the set of data format criteria, generating a second version of the first patient record based on a format transformation heuristic, wherein the format transformation heuristic comprises a data size reduction operation.

21. The medium of claim 1, the operations further comprising:
obtaining a text entry of the first patient record;
using a natural language processing system to determine a first health condition label based on the text entry;
determining whether the first health condition label is associated with the first patient record;
in response to a determination that the first health condition label is not associated with the first patient record, associating the first health condition label with the first patient record;
associating a second health condition label with the first patient record using a rule of a symbolic artificial intelligence system, wherein using the rule comprises determining whether a quantitative value satisfies a threshold of the rule;
associating a third health condition label with the first patient record using a neural network that takes, as inputs, the first health condition label and the second health condition label; and
updating the priority score based on the first health condition label, second health condition label, and third health condition label.

22. A method, comprising:
obtaining, with a computing system, a population of patient records, wherein a count of the population of patient records is greater than or equal to 10,000 records, and wherein:
each respective record of the population of patient records comprises a respective set of time values, a respective set of health scores associated with a respective patient identifier, and a respective healthcare resource identifier, and
each time value of the respective set of time values indicates an event occurrence time, wherein the event occurrence time is associated with an update to the respective set of health scores;
assigning, with the computing system, a plurality of priority scores to the population of patient records using a prioritization heuristic based on a prioritization criterion, wherein the population of patient records comprises a first patient record and a second patient record, and wherein using the prioritization heuristic comprises:
determining a first elapsed time based on a first time value of the first patient record, wherein the first patient record comprises a first health score, and wherein the first time value and the first health score are associated with the prioritization criterion;
determining a first priority score associated with the first patient record based on the first elapsed time and the first health score, wherein the plurality of priority scores comprises the first priority score; and
determining a second priority score associated with the second patient record based on a second time value and a second health score, wherein the second patient record comprises the second time value and the second health score, and wherein the second time value and the second health score are associated with the prioritization criterion, and wherein the plurality of priority scores comprises the second priority score;
sorting, with the computing system, the plurality of priority scores into a sequence of priority scores to determine a sequence of records from the population of patient records, wherein the first priority score is lower in the sequence of priority scores than the second priority score;
obtaining, with the computing system, a utilization schedule of a healthcare resource based on a resource identifier, wherein the resource identifier is determined based on a record selected from the sequence of records; and
displaying, with the computing system, values associated with the sequence of records in a user interface, wherein:
the first patient record identifies a first person,
the values comprise a name of the first person and a contact value of the first person,
the user interface comprises a first user interface element to indicate whether the first person had already been contacted within a threshold period of time,
the user interface comprises a second user interface element that, when interacted with, causes the user interface to dynamically populate the utilization schedule,
the utilization schedule is displayed concurrently with the contact value of the first person on a same screen of the user interface, and
interaction with an element of the utilization schedule causes the update of scheduling data stored in an external application via an application program interface.

* * * * *